(12) United States Patent
Schuster et al.

(10) Patent No.: US 6,877,376 B1
(45) Date of Patent: Apr. 12, 2005

(54) APPARATUS, SYSTEMS, AND METHODS FOR ULTRASOUND SYNTHETIC APERATURE FOCUSING

(75) Inventors: George J. Schuster, Kennewick, WA (US); Susan L. Crawford, Richland, WA (US); Steven R. Doctor, Richland, WA (US); Robert V. Harris, Pasco, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 10/339,358

(22) Filed: Jan. 8, 2003

Related U.S. Application Data
(60) Provisional application No. 60/347,684, filed on Jan. 8, 2002.

(51) Int. Cl.[7] ............................................. G01N 29/06
(52) U.S. Cl. .......................................... 73/602; 73/620
(58) Field of Search ................... 73/602, 620; 600/437, 600/443, 444, 643

(56) References Cited

U.S. PATENT DOCUMENTS

| | | | |
|---|---|---|---|
| 4,258,574 A | | 3/1981 | Hildebrand et al. |
| 4,557,146 A | | 12/1985 | Buffington et al. |
| 4,841,489 A | | 6/1989 | Ozaki et al. |
| 4,889,122 A | | 12/1989 | Watmough et al. |
| 4,953,147 A | | 8/1990 | Cobb |
| 5,186,177 A | | 2/1993 | O'Donnell et al. |
| 5,454,045 A | | 9/1995 | Perkins et al. |
| 5,465,722 A | | 11/1995 | Fort et al. |
| 5,549,002 A | | 8/1996 | Howard et al. |
| 5,646,351 A | | 7/1997 | Good et al. |
| 5,801,312 A | * | 9/1998 | Lorraine et al. ............... 73/602 |
| 5,897,501 A | | 4/1999 | Wildes et al. |
| 6,099,475 A | | 8/2000 | Seward et al. |
| 6,128,092 A | | 10/2000 | Levesque et al. |
| 6,449,821 B1 | | 9/2002 | Sudol et al. |
| 6,695,778 B2 | * | 2/2004 | Golland et al. ............. 600/437 |

OTHER PUBLICATIONS

G. J. Schuster and S.R. Doctor, *Use of SAFT–UT in Characterizing Fabrication Flaws in Nuclear Reactor Pressure Vessels*, Pacific Northwest Nat. Laboratory, Richland, WA, Nov. 2001.

* cited by examiner

*Primary Examiner*—Hezron Williams
*Assistant Examiner*—Nashmiya Fayyaz
(74) *Attorney, Agent, or Firm*—Woodard, Emhardt, Moriarty, McNett & Henry LLP

(57) ABSTRACT

One form of the present invention is a technique for interrogating a sample with ultrasound which includes: generating ultrasonic energy data corresponding to a volume of a sample and performing a synthetic aperture focusing technique on the ultrasonic energy data. The synthetic aperture focusing technique includes: defining a number of hyperbolic surfaces which extend through the volume at different depths and a corresponding number of multiple element accumulation vectors, performing a focused element calculation procedure for a group of vectors which are representative of the interior of a designated aperture, performing another focused element calculation procedure for vectors corresponding to the boundary of the aperture, and providing an image corresponding to features of the sample in accordance with the synthetic aperture focusing technique.

11 Claims, 20 Drawing Sheets

APPARATUS, SYSTEMS, AND METHODS FOR ULTRASOUND SYNTHETIC APERATURE FOCUSING

CROSS-REFERENCE TO RELATED APPLICATIONS

The present application claims the benefit of U.S. Provisional Patent Application No. 60/347,684 filed 8 Jan. 2002, which is hereby incorporated by reference in its entirety.

GOVERNMENT RIGHTS

This invention was made with Government support under Contract DE-AC06-76R1-1830 awarded by the U.S. Department of Energy. The Government has certain rights in the invention.

BACKGROUND

The present invention relates to apparatus and methods for ultrasound signal processing, and more specifically, but not exclusively, relates to techniques for synthetic aperture focusing of ultrasound systems.

Existing Synthetic Aperture Focusing Techniques (SAFTs) for ultrasound systems typically sum all sampled volume elements that fall on a predicted hyperbolic surface to a single accumulator to produce a fully focused volume element, and this completed summation is recorded into a second sampled volume of focused volume elements. U.S. Pat. Nos. 6,128,092; 5,465,722; and 4,841,489 are cited as sources of further information concerning SAFT for ultrasound systems.

Generally for SAFT routines, if the sampled volume is cubic with n samples on a side, then the order of magnitude of the processing task is $n^5$. SAFT inspections can generate data volumes with $10^9$ total volume elements, i.e. cubes with one thousand samples on a side. If worst-case complexity is assumed, $10^{15}$ summations can result.

When the summation is restricted to a synthetic aperture the complexity of the computation can sometimes be reduced by as much as a factor of 10; however, real-time performance at this level of complexity is still often difficult to achieve with cost-effective processing equipment. Frequently, such performance is often desired for imaging and other interrogation synthetic aperture focusing applications utilizing ultrasound. Consequently, SAFT routines sometimes include skip logic to give reasonable performance by omitting the focusing of volume elements with low responses. Unfortunately, this approach may still offer unacceptable results. Accordingly, better processing techniques and/or equipment, such as transducer devices better suited to SAFT, are needed to advance SAFT-based ultrasound systems.

SUMMARY

One embodiment of the present invention includes a unique synthetic aperture focusing technique for an ultrasound system. Other embodiments include unique apparatus, devices, systems, and methods that relate to ultrasound signal generation, reception, and/or processing.

A further embodiment includes a housing defining an interior and including a base with a generally planar face operable to couple to a sample to be ultrasonically interrogated and an ultrasonic transducer including a curved active element that is generally symmetric about an axis. The transducer is coupled to the housing to position the active element in the interior with the axis intersecting a plane coextensive with the face at an oblique angle.

Another embodiment includes a transducer device operable to interrogate a sample with ultrasound that includes one or more active elements with a spherical concave or convex face and one or more processors responsive to ultrasound interrogation signals from the transducer device to perform a synthetic aperture focusing technique relative to a sample volume by calculating a plurality of sums corresponding to a plurality of hyperbolic surfaces extending through the sample volume at different relative depths. An output device can also be included that is responsive to the one or more processors to generate an image of the sample in accordance with the synthetic aperture focusing technique.

Still another embodiment includes: interrogating a sample with ultrasound; generating data corresponding to ultrasound returned by a volume of the sample in response to this interrogation; performing a synthetic aperture focusing technique that defines a number hyperbolic surfaces extending through the volume at different depths and a corresponding number of multiple element accumulation vectors; and providing an image corresponding to the sample in accordance with the synthetic aperture focusing technique.

Yet another embodiment includes a device carrying logic executable by one or more processors to perform a synthetic aperture focusing technique including: defining a number hyperbolic surfaces extending through an ultrasonic interrogation sample volume at different depths and a corresponding number of multiple element accumulation vectors, executing one focused element calculation procedure for a group of the vectors representative of the interior of a designated aperture in correspondence to a cross section, and executing another focused element calculation procedure for vectors corresponding to a boundary of the aperture.

One object of the present invention is to provide a unique synthetic aperture focusing technique for an ultrasound system.

Another object of the present invention is to provide a unique apparatus, device, system, or method that relates to ultrasound signal generation, reception, and/or processing.

Further objects, forms, embodiments, features, aspects, benefits, and advantages of the present invention shall become apparent from the detailed drawings and descriptions provided herein.

BRIEF DESCRIPTION OF THE DRAWING

In the following figures, like reference numerals represent like features. In some cases, the figures or selected features thereof are not drawn to scale to enhance clarity.

DETAILED DESCRIPTION OF SELECTED EMBODIMENTS

Figure 1:
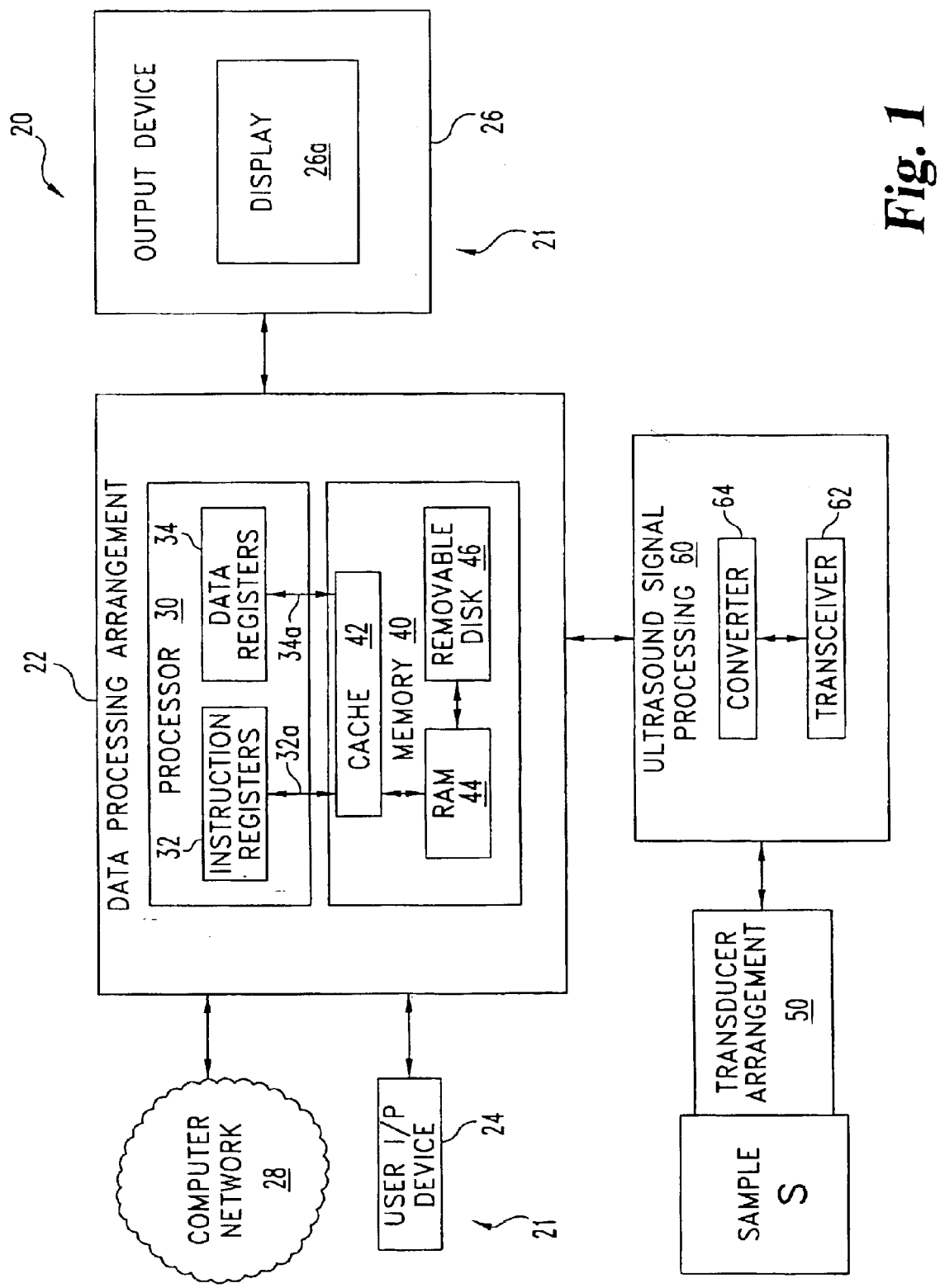
FIG. 1 is a diagrammatic view of an ultrasound system.

While the present invention may be embodied in many different forms, for the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

One embodiment of the present invention is a unique real-time ultrasound SAFT imaging technique that can utilize less expensive processing equipment than current approaches. As used herein "real-time" for SAFT refers to the completion of focusing in less than or equal to the amount of time needed to acquire the ultrasound interrogation data. Additionally or alternatively, another embodiment includes one or more unique long-range transducer devices according to the present application. Still other embodiments combine these features and/or include different unique aspects of the present application.

FIG. 1 depicts ultrasound system 20 of one embodiment of the present invention. System 20 includes computer equipment 21. Equipment 21 includes data processing arrangement 22, at least one user input (I/P) device 24, and at least one user output device 26. Input device 24 is operatively coupled to arrangement 22 to provide user input thereto, and can include one or more of a keyboard, a mouse, a trackball, a light pen, a digitizing tablet, a voice recognition subsystem, and/or different input arrangement as would occur to those skilled in the art. Output device 26 is operatively coupled to arrangement 22 to output graphic imagery. Output device 26 includes a standard graphic computer monitor display 26a and additionally can include a printer, an aural output system, and/or different output device type as would occur to those skilled in the art. In one embodiment, computer monitor display 26a is of a Cathode Ray Tube (CRT), Liquid Crystal Display (LCD), plasma, or different graphic computer monitor display type as would occur to those skilled in the art. Computer equipment 21 can be provided as a standard desktop computer or other suitable computer configuration.

Arrangement 22 includes at least one processor 30 having one or more instruction registers 32 and data registers 34. Processor 30 can include one or more other registers, logic, and the like as required to operate in the manner described herein. In one form, processor 30 is programmed with software instructions that are executed to perform various desired operations. In other forms, some or all of the logic executed by processor 30 is in accordance with firmware instructions; dedicated hardware, such as hardwired digital and/or analog circuitry; and/or using such different techniques as would occur to one skilled in the art. In one embodiment, processor 30 is programmable and includes at least one Central Processing Unit (CPU) with at least one Arithmetic Logic Unit (ALU) and is of a standard, commercially available, solid-state integrated circuit type. For embodiments of arrangement 22 that include multiple processors 30 and/or one or more processors 30 with multiple CPUs, a parallel and/or pipeline processing arrangement can optionally be utilized.

Arrangement 22 also includes memory 40 coupled to processor 30. Memory 40 includes associative high-speed cache 42, RAM (Random Access Memory) 44 and removable/portable nonvolatile mass storage memory device 46. Cache 42 is of a solid-state electronic static memory device form. RAM 44 can also be of a solid-state electronic form of either a static or dynamic type and/or can be volatile or nonvolatile. Device 46 can be an optical disk (such as a CD ROM or DVD); an electromagnetically encoded removable/portable hard or floppy disk, a nonvolatile solid-state integrated circuit memory cartridge or card, a bubble memory cartridge, an electromagnetic tape, or a different removable/portable form as would occur to those skilled in the art. Memory 40 can further include other memory types as would occur to those skilled in the art.

Cache 42 is operatively coupled to the one or more instruction registers 32 of processor 30 by instruction pipeline 32a and is also operatively coupled to the one or more data registers of processor 30 by data pipeline 34a. Cache 42 is also coupled to RAM 44 by bus 42a in a standard manner. Equipment 21 can include other devices such as one or more clocks, filters, signal conditioners, scanning subsystems, format converters (such as analog-to-digital and/or digital-to-analog converters), buffers, controllers, power supplies, and the like as would occur to those skilled in the art to implement the present invention.

System 20 also includes computer network 28 that can include a Local Area Network (LAN); Wide Area Network (WAN), such as the Internet; another type as would occur to those skilled in the art; or a combination of these. Network 28 is operatively coupled to arrangement 22 of computer equipment 21 in a standard manner. One or more remote computers (not shown) can be operatively coupled to equipment 21 via network 28 to remotely operate and/or control system 20, participate in distributed processing with equipment 21, and/or participate in a client/server relationship with equipment 21.

System 20 also includes ultrasound transducer arrangement 50 shown in relation to sample S. Sample S is provided to be interrogated with ultrasound energy by system 20. Arrangement 50 includes one or more ultrasound transducers. At least one transducer of arrangement 50 is operable to transmit ultrasound energy through sample S and at least one transducer of arrangement 50 is operable to receive ultrasound energy from sample S returned in response to the transmitted ultrasound energy. Accordingly, for an embodiment in which arrangement 50 only includes a single transducer, such transducer is of a type that is configured to both transmit and receive ultrasound. Another embodiment includes an array of ultrasound transducers each configured to transmit and receive. Still another embodiment includes an array of transducers that are each designated to receive only or transmit only. Nonlimiting examples of transducer devices suitable for use with arrangement 50 are further described in connection with FIGS. 6–15 hereinafter.

Arrangement 50 is operatively coupled to ultrasound signal processing and control equipment 60. Equipment 60 includes at least transceiver 62 operatively coupled to signal format converter 64. Equipment 60 is operatively coupled to equipment 21 to communicate data corresponding to an ultrasound interrogation of sample S. Arrangement 50 is responsive to an electrical signal transmitted from transceiver 62 to transmit ultrasound energy to sample S with one or more of its transducers. Also, arrangement 50 responds to ultrasound energy detected with one or more of its transducers to generate a corresponding electrical signal that is received with transceiver 62.

Transceiver 62 includes one or more electrical signal receivers and transmitters as desired to complement the configuration of arrangement 50. Converter 64 includes circuitry to convert electrical signals received from transceiver 62 into a format suitable for storage in memory 40. Typically, converter 64 includes at least one analog-to-digital (A/D) converter for this purpose and may include other format conversion circuitry such as a codec or the like as desired. Equipment 60 can include other circuitry and devices desired to operate arrangement 50 such as one or more clocks, filters, signal conditioners, scanning subsystems, memories, buffers, programmable controllers, power supplies, and the like as would occur to those skilled in the art to implement the present invention.

Figure 2:
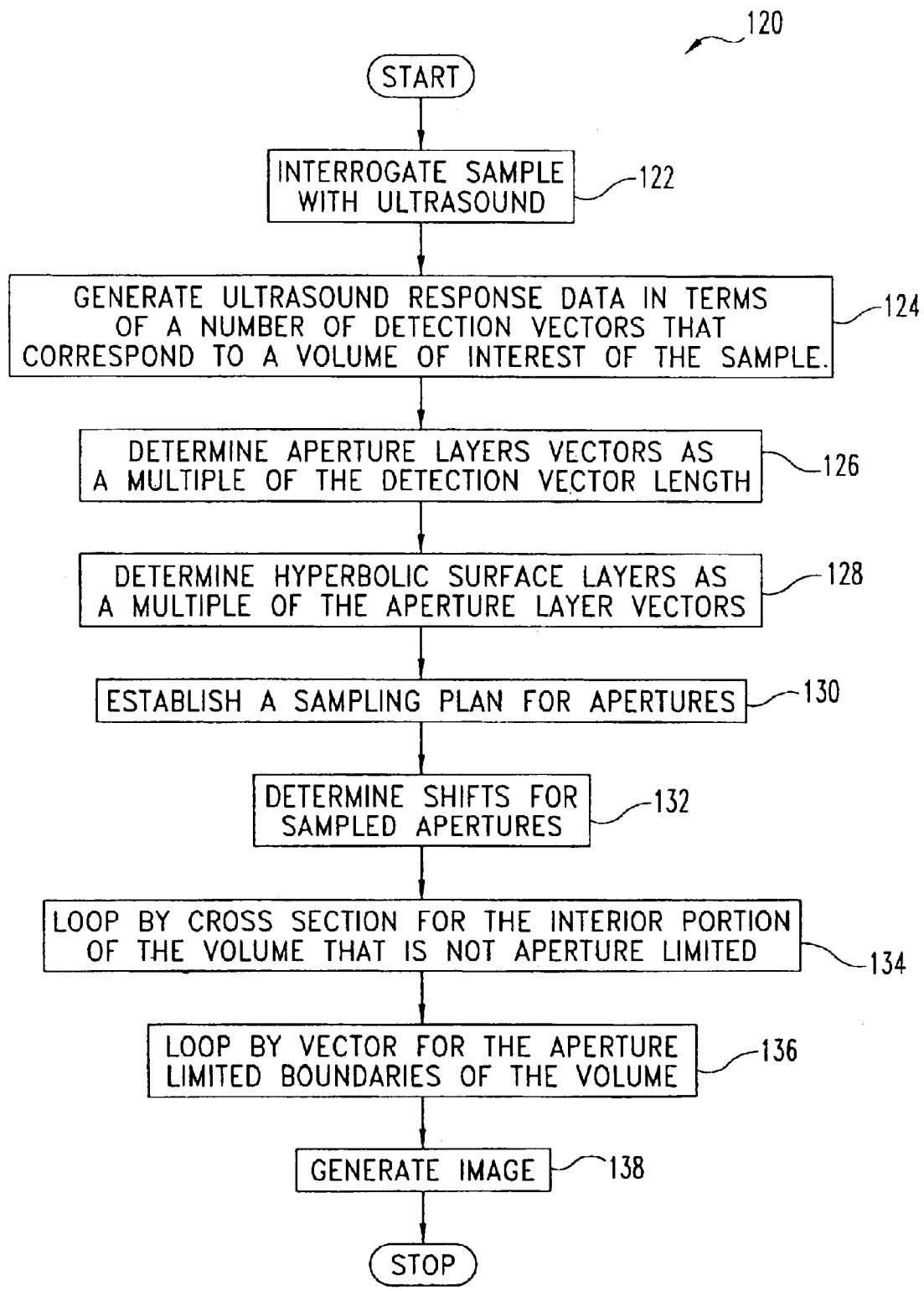
FIG. 2 provides a flowchart of a synthetic aperture focusing routine that can be implemented with the system of FIG. 1.
Figure 3:
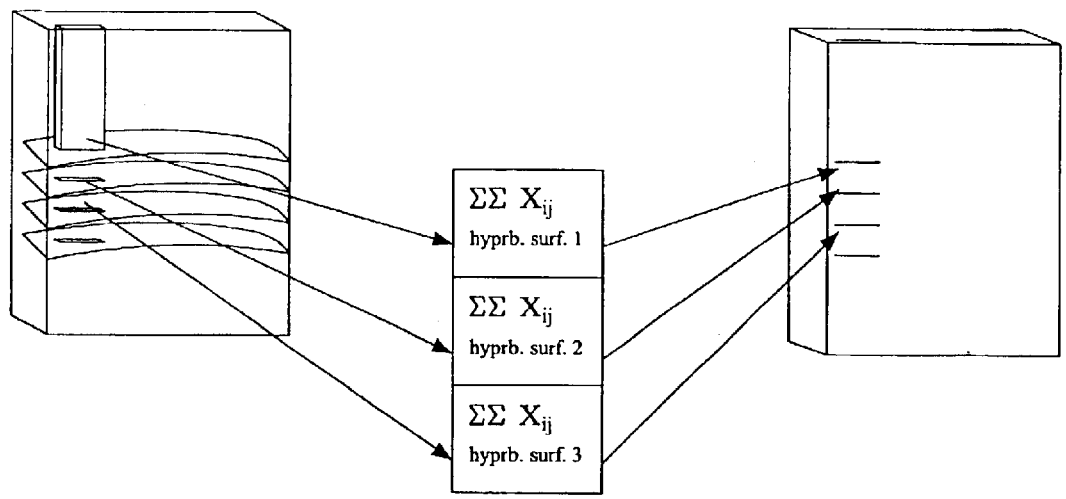
FIG. 3 is a diagram further illustrating certain operational aspects of the routine of FIG. 2.

FIG. 2 presents a flowchart of SAFT routine 120 of the present invention. Routine 120 is implemented system 20 and variations and alternatives thereof as describe herein. In other embodiments, routine 120 can be implemented with a different system as would occur to those skilled in the art. Existing SAFT algorithms sum sample points along a hyperbolic surface at a given depth in the sample to provide a focused element at that depth. This process is repeated for each of a number of hyperbolic surfaces at different depths. In contrast, routine 120 simultaneously sums sample points along each of a stack of hyperbolic surfaces corresponding to different depths in a sample volume to accumulation vectors to produce vectors of fully focused volume elements. FIG. 3 represents this operation in graphical form for a single representative vector. The left hand side of FIG. 3 shows a representation of a sampled volume with a stack of similar hyperbolic surfaces within the volume. A vector of volume elements that fall on these surfaces is summed into an accumulation vector represented in the middle of FIG. 3. The completed summation vector is recorded into a second sampled volume of focused volume elements as shown on the right side of FIG. 3. In another aspect, routine 120 limits the portion of each hyperbolic surface utilized to a circular or elliptical area centered on the ultrasonic energy beam used for interrogation—typically resulting in unexpected performance advantages.

Returning to FIG. 2, routine 120 starts with stage 122 in which sample S is interrogated with ultrasonic energy in a standard manner. In stage 124, ultrasound energy returned in response to the interrogation of stage 122 is utilized to generate time-of flight data in terms of a number of detection vectors dv. These detection vectors correspond to a volume of interest of sample S.

Routine 120 proceeds from stage 124 to stage 126. In stage 126, a number of aperture layers in the volume are determined as an aperture vector av. The length (number of layers) in vector av is determined as a multiple of the detection vector dv length and the length of data registers 34 (processing vector rv) for the type of processor 30 utilized. For a given half beam width angle, $\theta$, the relationship between the aperture radius $r_\lambda$ and depth "z" is given by equation (1) as follows:

$$r_x = z \tan \theta \tag{1}$$

This relationship can be approximated by a set of constant radius layers where the error "e" in the approximation is defined by equation (2) as follows:

$$e = (z_2 - z_1) \tan \theta \tag{2}$$

The maximum thickness of the constant radius layers can be expressed using an allowable error term defined as a fraction of the sampling interval per equation (3) as follows:

$$t_{a,\max} = \frac{c\Delta x}{\tan \theta} \tag{3}$$

Finally, the aperture layer thickness can be made a multiple of both the detection vector, $t_{dv}$, and the processor vector register length, $t_{rv}$, as defined by equation (4) that follows:

$$t_{rv} = \text{Whole}\left(\frac{t_{h,\max}}{L.C.M.(t_{dv}, t_{rv})}\right) \times (L.C.M.(t_{dv}, t_{rv})) \tag{4}$$

where the operator Whole ( ) returns the truncated whole number of its operand in parentheses and the operator L.C.M.( ) returns the least common multiple of its operands in parentheses.

Routine 120 proceeds from stage 126 to stage 128. In stage 128, hyperbolic surface layers through the volume of interest are determined as a multiple of the length of the aperture layer vectors av. First, find the layer thickness, $t_{h,\max}$, where all hyperbolae within $t_{h,\max}$ differ by less than a predefined fraction (by way of nonlimiting example, a tenth) of a wavelength of the ultrasound acoustic waveform used for interrogation in stage 122. Given the start depth, $d_1$, find the stop depth, $d_2$, for the layer of hyperbolae that differ by less than a given fraction, $c_h$, of this wavelength at the edge of the aperture. The expression to solve is given by equation (5) as follows:

$$z_1 + t_{h,\max} + c_h \lambda = z_2$$

A hyperbola has a depth, $z_a$, at the edge of the aperture as given by equation (6) as follows:

$$z_a = \sqrt{d^2 + x^2} = (d^2 + d^2 \tan^2 \theta)^{1/2}$$

Figure 4:
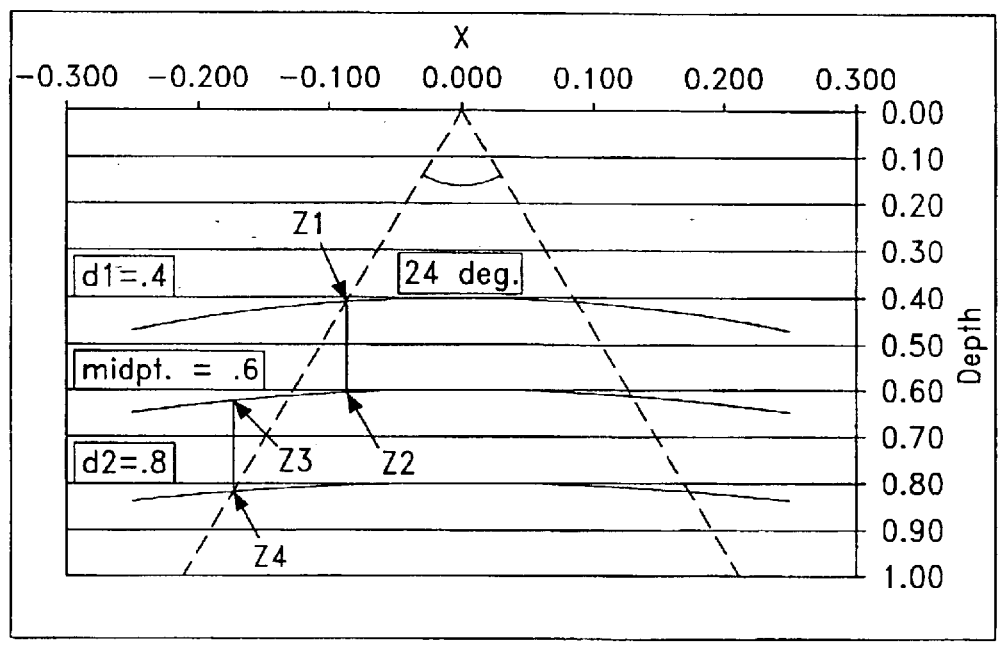
FIGS. 4 and 5 diagrammatically depict certain aspects of the routine of FIG. 2.

FIG. 4 illustrates this approach to estimating the maximum hyperbola layer thickness relative to a bipolar index along the x direction. The hyperbola estimate uses the midpoint of the layer and the layer thickness is found by using an error constraint. Using this constraint, the expression for the top of the layer is given by equation (7) as follows:

$$(d_1^2+d_1^2 \tan^2 \theta)^{1/2}+(d_m-d_1)+c_h\lambda=(d_m^2+d_1^2 \tan^2 \theta)^{1/2} \quad (7)$$

The expression for the bottom of the layer is given by equation (8) as follows:

$$(d_m^2+d_2^2 \tan^2 \theta)^{1/2}+(d_2-d_m)+c_h\lambda=(d_2^2+d_2^2 \tan^2 \theta)^{1/2} \quad (8)$$

So a solution results by finding $d_2$ given $d_1$ where $\theta$ is half the beam width angle. The hyperbola layer thickness can be made a multiple of the aperture vector length (in terms of $t_{av}$) as follows in equation (9):

$$t_{hv} = \text{Whole}\left(\frac{t_{h,\max}}{t_{av}}\right) \times t_{av} \quad (9)$$

Routine 120 proceeds from stage 128 to stage 130. In stage 130, a sampling plan is established for the desired aperture. The volume of interest is defined in terms of discrete samples in three dimensions. The samples are indexed with indices i, j, and k corresponding to the x, y and z Cartesian coordinates (and directions), respectively. Given a sampled volume of responses $R_{ijk}$ then for all depths $d_k$ of the volume find all sample positions that are in an aperture. For a circular aperture, the following equation (10) applies:

$$r_k = d_k \tan \theta \quad (10)$$

Given n aperture layers and aperture layer thickness $t_{av}$, create a stop index that is a positive number of sample positions in the y direction from the center sample position for each of the aperture layers. Also, for each aperture layer and for each sample position along the y direction, create a stop index along the x direction. Pseudocode for this subroutine is as follows:

```
For each aperture layer
    Get the number of Z samples to the layer midpoint
    Calculate the depth of midpoint to the layer
    Calculate the length of the aperture for the layer
    Set the Y aperture boundary index for the layer
    For each Y position in this layer
        Calculate the length of the aperture for this Y position
        Set the X aperture boundary index for this Y position
    End loop
End loop
```

Routine 120 proceeds from stage 130 to stage 132. In stage 132, shifts are calculated for the sampled apertures. Defining the samples in the aperture layers with bipolar indices, find the sample shifts, $n_{ijk}$, for all depths and sample positions in the aperture as given by equations (11) and (12) that follow:

$$n_{ijk} = \frac{Z_{ijk}}{\Delta z} - \frac{d_k}{\Delta z} \quad (11)$$

where:

$$Z_{ijk} = (d_k^2 + x_i^2 + y_j^2)^{1/2} \quad (12)$$

Figure 5:
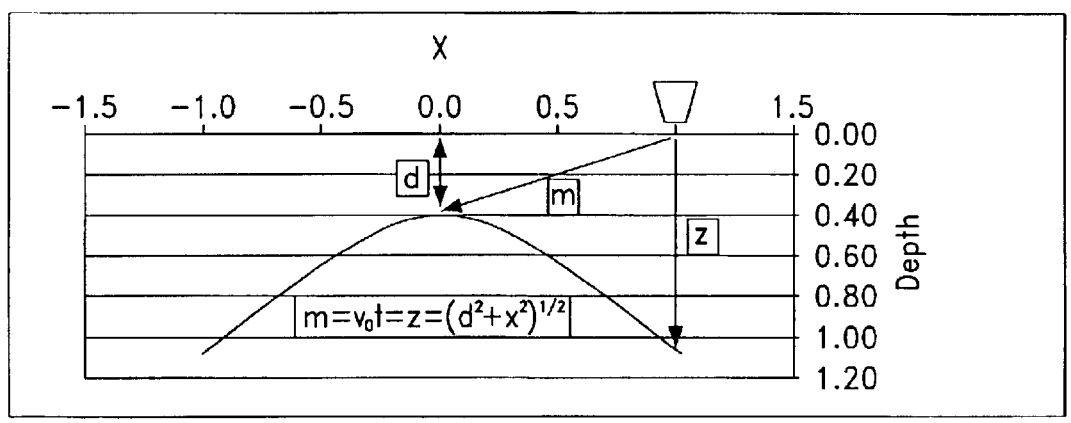

$\Delta z$ is the distance between volume elements in the z direction; $d_k$ is the depth of the volume element of interest k samples from the surface; $x_i = i \, \Delta x$ with i being the bipolar index from the aperture and $\Delta x$ being the distance between volume elements in the x direction; and $y_j = j \, \Delta y$ with j being the bipolar index in the y direction and $\Delta y$ being the distance between volume elements in the y direction. FIG. 5 illustrates certain aspects of these determinations.

The depth range is divided into equally spaced layers of approximately equivalent hyperbolae. The size of these layers is given by $t_{hv}$. A bipolar indexed array is created for each shift layer. In the shift array, for any layer, there is a shift in depth samples for all responses in the aperture. The size of the shift array, for any layer, uses the aperture at the bottom of the layer. Pseudocode for this subroutine is as follows:

```
For all hyperbola layers
    Get depth of the midpoint in the hyperbola layer
    For all sample positions in the aperture
        Calculate the depth shift
    End loop
End loop
```

Sampled aperture layers improve the focusing algorithm by sampling the aperture across its entire diameter while skipping selected data in it. It should be appreciated that the diameter of the aperture generally determines resolution, so this sampling approach should not cause significant degradation. The scanning is performed on half-wavelength steps but not all points in the aperture will be accumulated in the summation. Each step in the scan is focused, giving a resultant image with half wavelength spacing.

The aperture sampling algorithm provides indices for each of the quantized shifts in the hyperbolic surface within the aperture for the layer being considered. Accordingly, an approach is provided to perform any explicit type conversion and data alignment of vector data registers and the execution pipeline. Pseudocode for this subroutine is as follows:

```
For each aperture layer
    For each shift on the hyperbolic surface for this aperture layer
        Create the aperture sampling indices
    End loop
End loop
```

Given the aperture sampling indices for each shift in the aperture layers, find the change in address to the coherent responses for the volume element of interest. A bipolar total shift algorithm can be utilized. In one form, an array of signed 32 bit integers is used to represent address changes. An address is given by equation (13) as follows:

$$A_{ij} = n_s(jn_x+i)+n_h \quad (13)$$

where $n_s$ is the number of samples in a scan, j and i are the bipolar indices from the aperture, and $n_x$ is the number of steps in the scan direction. The hyperbolic shift, $n_h$, is a constant for each sampled aperture index.

From stage 132, routine 120 continues with subroutine 134. In subroutine 134, a nested loop procedure is performed to sum the data by cross section for an interior portion of the volume that is not aperture limited. Correspondingly, a cross section of accumulator vectors rv is used to focus a cross section of volume elements. In this "by cross section" approach, all points on a stack of similar hyperbolic surfaces are summed to an accumulation plane to produce a plane of fully focused volume elements. A stack of similar hyperbolic surfaces within the unfocused volume is summed into an accumulation plane. The completed summation plane is recorded into a second sampled volume of focused volume elements. The summation is performed with subroutine 134 using a boundary definition for the samples in the aperture. To follow the hyperbolic surface, layers of similar hyperbolae are used. Pseudocode for one form of an eight-loop design of subroutine 134 is as follows:

```
For all y steps of the cross section
    For all x steps of the cross section
        or all z steps of the cross section
            If this cross section cannot be skipped
                For each shift in the sampled aperture
                    For all y sample positions with this shift in the
                        aperture
                            For all x sample positions with this shift in
                                the aperture
                                    For all x elements in the cross section
                                        For all z elements in the cross
                                            section
                                                Add the shifted response to
                                                    the accumulator
                                            End loop
                                        End loop
                                    End loop
                                End loop
                            End loop
                            Detect, normalize, and, store one cross section
            End if
        End loop
    End loop
End loop
```

From subroutine 134, routine 120 continues with subroutine 136. In subroutine 136, a nested loop by-vector summation procedure is performed that utilizes skip and aperture sampling for the aperture limited sides of the volume. A vector of accumulators is utilized to focus a vector of volume elements. The summation for subroutine 136 is performed using a boundary definition for the samples in the aperture. To follow the hyperbolic surface, layers of similar hyperbolae are used. Pseudocode for one form of a seven-loop design of subroutine 136 is as follows:

```
For all y steps of the accumulation vector
    For all x steps of the accumulation vector
        For all z steps of the accumulation vector
            If this vector cannot be skipped
                For each shift-annulus in the sampled aperture
                    For all y sample positions with this shift in the
                        aperture
                            For all x sample positions with this shift in
                                the aperture
                                    For all elements in the vector
                                        Add the shifted response to the
                                            accumulator
                                    End loop
                                End loop
                            End loop
                        End loop
                        Detect, normalize, and, store one vector
            End if
        End loop
    End loop
End loop
```

From subroutine 136, routine 120 continues with stage 138. In stage 138 an image is rendered that corresponds to the resulting volume of focused elements using standard techniques. Such image can be used to detect defects beneath the surface of a sample. Routine 120 then halts.

Alternatively or additionally, SAFT can be performed in accordance with another embodiment of the present invention by utilizing a "by sub-volume" routine. For this routine, all points on a stack of similar hyperbolic surfaces are summed to an accumulation volume to produce a sub-volume of fully focused volume elements. A stack of similar hyperbolic surfaces within the unfocused volume is summed into an accumulation sub-volume. The completed summation sub-volume is recorded into a second sampled volume of focused volume elements.

It has been found that SAFT routine 120 can be executed in a manner that facilitates near real-time operation with less expensive computing equipment than other SAFT-based systems. In one aspect of this embodiment, a low cache miss rate and/or a high utilization of specific CPU instructions are beneficial.

Referring to system 20 of FIG. 1, throughput of pipelines 32a and 34a, and bus 42a of computing equipment 21 typically constrain the speed for processing SAFT data from ultrasound signal control equipment 60. Generally it is desirable that bus 42a be minimally used to improve processing speed. In contrast, instruction pipeline 32a should stay full (maximum use) and data pipeline 34a should use the full bandwidth without transmitting unwanted data. For certain arrangements of equipment 21, cache 42 provides data to registers 34 at a maximum the clock rate of processor 30 provided that the SAFT implementation does not generate high cache miss fraction. For existing SAFT algorithms that operate on a "by volume element" with skip logic, it has been found that a high cache miss fraction of 1.0 can exist, with the corresponding penalty for a cache miss being 20 CPU cycles or more. Accordingly, the performance of this existing SAFT algorithm does not scale well. In contrast, certain embodiments of a SAFT routine according to the present application, address space changes are greatly reduced giving relatively low cache miss fractions, and therefore improving scalability.

Instruction sets for certain processor can make more efficient use of the data pipeline relative to other less sophisticated processor types. Intel Corporation's Pentium III Zeon, has instruction sets that are specific to its corresponding CPU type. Large increases (a factor of 10 or more) in the performance of certain embodiments of a SAFT routine of the present application can be realized through routines better designed to use specific instruction sets. Moreover, this implementation can be extended to use multi-threading to scale the performance with the number of CPUs utilized.

Figure 17:
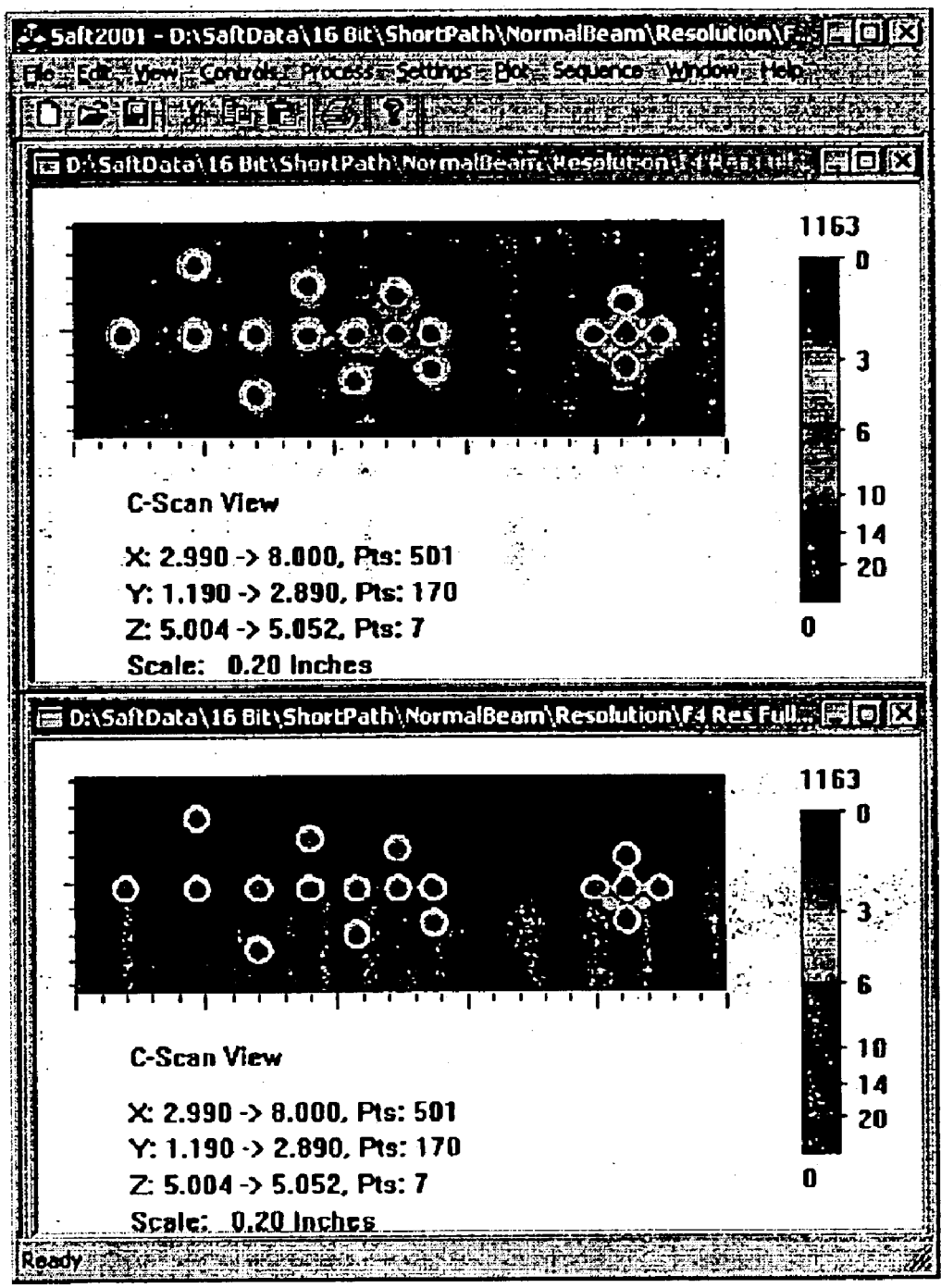

A comparative performance of the "by cross section" subroutine of stage 134 of routine 120 with summation on a horizontal plane, is shown in FIG. 17 for selected CPUs. Summation on a horizontal plane was used to test the performance of the "by cross section" algorithm for SAFT implementation. A Pentium 3 CPU with a clock rate of 800 MHz executed the algorithm at 650 million sums per second. Dual Pentium 3 CPUs executed at 1.25 billion sums per second. A Pentium 4 CPU with a clock rate of 1.7 GHz produced a summation rate of 2.25 billion sums per second. The performance of the existing SAFT algorithm is represented in the figure by measuring the summation rate on a horizontal surface: 20 million sums per second on all CPUs. Two CPUs were tested. A computer with dual CPUs was also used. The performance of a standard "by element" algorithm is shown for comparison.

Referring to FIGS. 6–15 various transducer configurations and devices are illustrated. These devices are particularly suitable for use in transducer arrangement 50 of system 20 when directed SAFT performance. Existing SAFT transducers tend to use small 6 mm diameter contact probes to generate the diverging beam. These probes are low power devices and limit the resolving power of SAFT. In contrast, for many near real-time SAFT applications, a long range transducer of relatively high power is desired. Also, generally for SAFT applications, divergence of the ultrasonic beam is desired so that the reconstruction can find time-of-flight shapes. The transducers illustrated include curved active elements to provide the desired divergence. In some embodiments, this curvature is defined by a convex face to be directed toward the sample, which is generally more appropriate for a rough or irregular sample surface. In other embodiments the curvature is defined by a concave face to be directed toward the sample, which is generally more appropriate for a sample surface that is relatively smooth and uniform.

Figure 6:
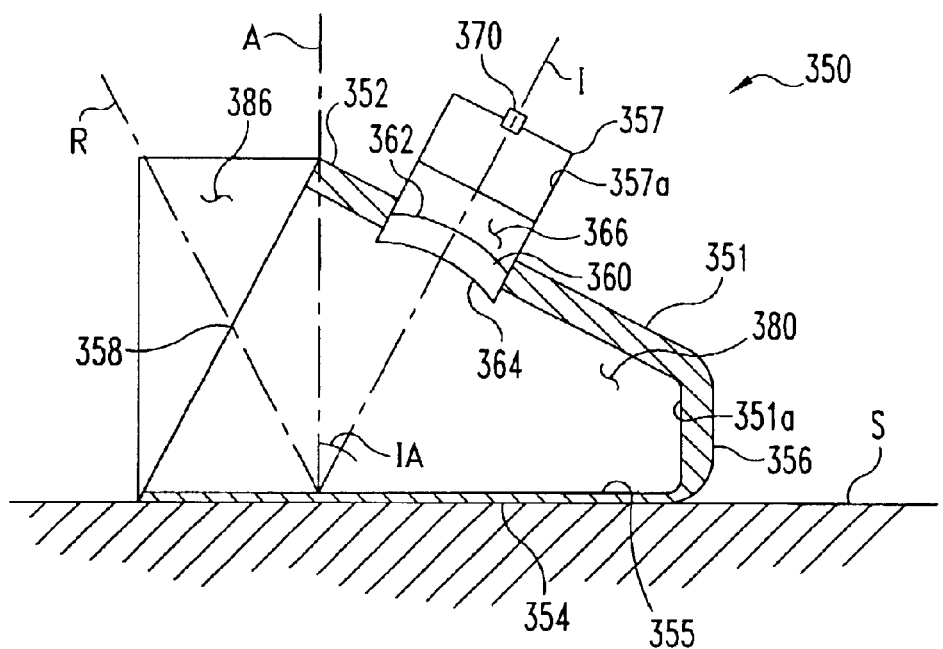
FIG. 6 is a partial diagrammatic side view of a first type of transducer device that can be included in the system of FIG. 1.

FIG. 6 schematically depicts ultrasonic transducer device 350. Device 350 includes casing or housing 351 defining an interior 351a. Housing 351 is comprised of upper shell 352 opposite a generally planar wear face 354 defined by housing base 355. Face 354 is configured to be coupled to sample S directly (as shown) or indirectly through a coupling material (not shown). Housing further includes wall portion 356 generally opposite wall portion 358. Device 350 also include transducer 357. Transducer 357 is coupled to upper shell 352 in a fixed relationship opposite base 355. Transducer 357 includes active element 360 having a curved convex face 362 opposite a curved concave face 364. Element 360 is spaced apart from base 355 and is positioned inside interior 351a to direct concave face 364 toward base 355 along axis I. Element 360 is generally symmetric about axis I which is at an oblique angle with a plane coextensive with wear face 354 and axis A; where axis A is coincident with the vertical direction and is approximately perpendicular with wear face 354. The incident angle of an ultrasound beam emanating from element 360 along axis I is designated as angle IA in FIG. 6. Element 360 can be circular, elliptical, rectangular or such other curvilinear and/or rectilinear shape about axis I.

A backing material 366 is provided to at least partially fill interior 357a of transducer 357. Device 350 includes connector 370 to which active element 360 is connected via appropriate cabling or wiring through interior 357a (not shown). Concave face 364 is in contact with ultrasonic energy coupling material 380 contained in interior 351a of housing 351 to enhance the transmission and detection of ultrasound through wear face 354. Wear face 354 is in contact with a surface of sample S. Device 350 further includes ultrasonic energy absorbing material 386 extending along at least part of wall portion 358 of housing 351. Material 386 is so positioned to absorb ultrasound reflections from base 355 and echoes traveling in the direction of axis R.

Figure 7:
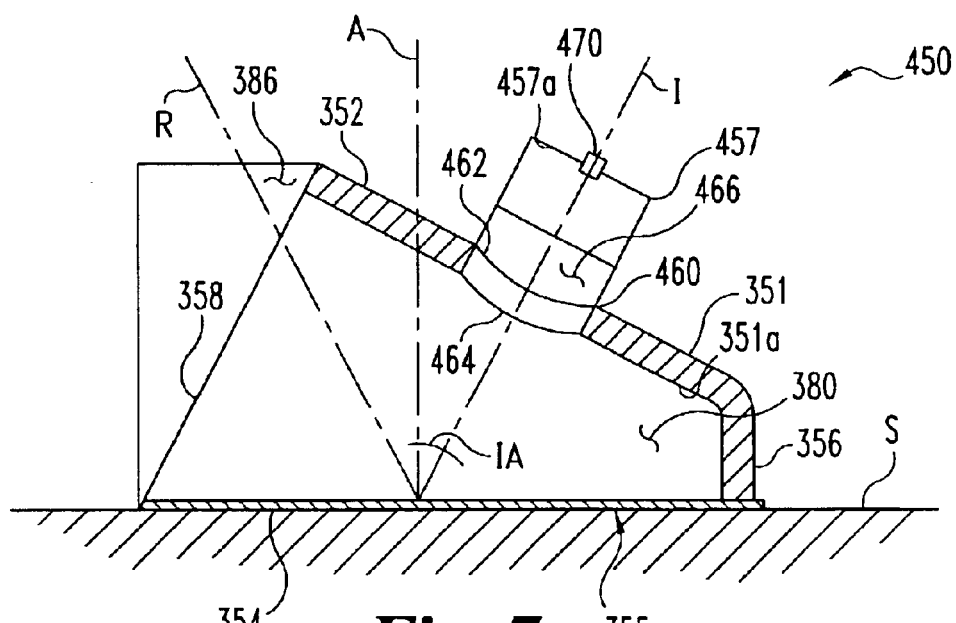
FIG. 7 is a partial diagrammatic side view of a second type of transducer device that can be included in the system of FIG. 1.

FIG. 7 schematically depicts ultrasonic transducer device 450. Device 450 includes casing or housing 351 defining interior 351a as described in connection with device 350; however, instead of transducer 357, device 450 includes transducer 457. Transducer 457 is coupled to upper shell 352 in a fixed relationship opposite base 355. Transducer 457 includes active element 460 having a curved concave face 462 opposite a curved convex face 464. Element 460 is spaced apart from base 355 and is positioned inside interior 351a to direct convex face 464 toward base 355 along axis I. Element 460 is generally symmetric about axis I which is at an oblique angle with a plane coextensive with wear face 354 and axis A. The incident angle of a diverging ultrasound beam emanating from element 460 along axis I is designated as angle IA in FIG. 7. Element 460 can be circular, elliptical, rectangular or such other curvilinear and/or rectilinear shape about axis I.

A backing material 366 is provided to at least partially fill interior 457a of transducer 457. Device 350 includes connector 470 to which active element 460 is connected via appropriate cabling or wiring through interior 457a (not shown). Convex face 364 is in contact with ultrasonic energy coupling material 380 contained in interior 351a of housing 351 to enhance the transmission and detection of ultrasound through wear face 354. Wear face 354 is in contact with a surface of sample S. Device 350 further includes ultrasonic energy absorbing material 386 extending along at least part of wall portion 358 of housing 351. Material 386 is so positioned to absorb ultrasound reflections from base 355 and echoes traveling in the direction of axis R.

Figure 8:
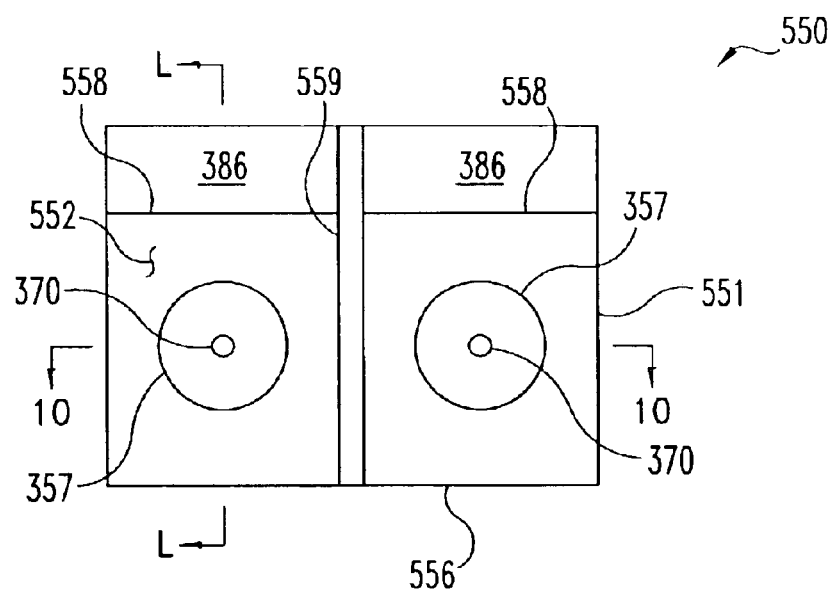
FIGS. 8 and 9 are partial diagrammatic views of a third type of transducer device that can be included in the system of FIG. 1.
Figure 9:
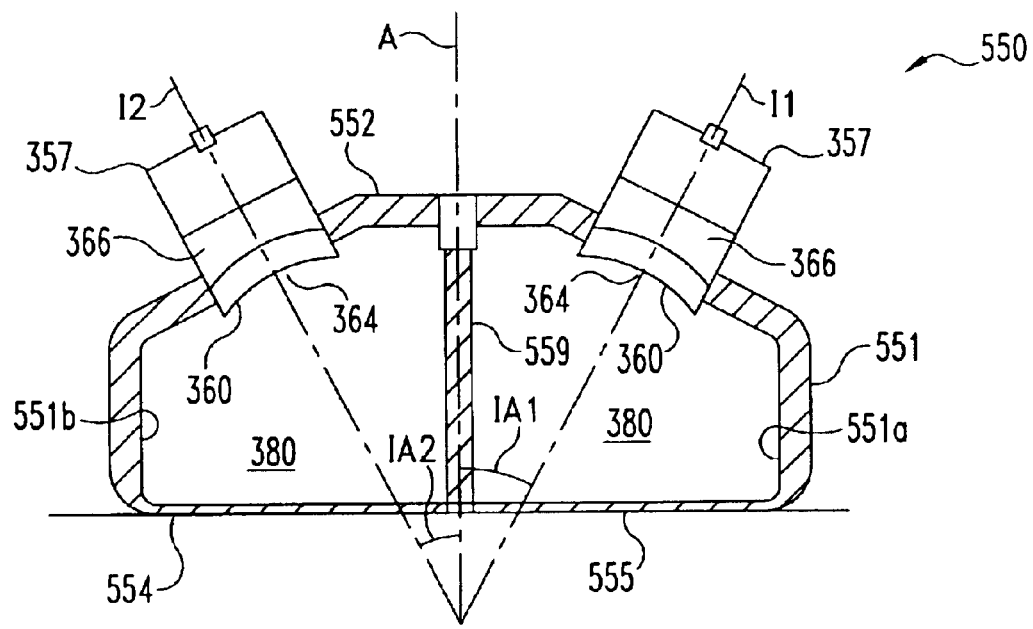

FIGS. 8 and 9 schematically depict dual element ultrasonic transducer device 550. Device 550 includes casing or housing 551 defining interior portions 551a and 551b. Housing 551 is comprised of upper shell 552 opposite a generally planar wear face 554 defined by housing base 555. Housing further includes wall portion 556 generally opposite wall portion 558. Device 550 also includes two transducers 357 each of the type previously described in connection with device 350 of FIG. 6. In FIG. 8, the view line L—L corresponds to a view that is the same as the schematic view of FIG. 6, except that reference numerals for housing 350 would be removed and replaced by corresponding reference numerals for housing 550.

In device 550, transducers 357 are both coupled to upper shell 552 in a fixed relationship opposite base 555. Housing 551 includes separating wall 559 that generally extends along axis A as shown in FIG. 9 to separate interior portions 551a and 551b from one another. One of transducers 357 is oriented to directed its curved concave face 364 along axis I1 to form incident angle IA1 with axis A, and the other of transducers 357 is oriented to direct its curved concave face 364 along axis I2 to form incident angle IA2 with axis A. Angles IA1 and IA2 are generally equal and opposite one another about axis A. Element 360 of each transducer 357 is positioned inside interior 351a or 351b to direct the corresponding concave face 364 toward base 355 along axis I1 or I2, respectively. Elements 360 of each transducer 357 are generally symmetric about the respective axes I1 and I2 which are each at an oblique angle with a plane of wear face 554 and axis A.

Concave face 364 of each element 360 is in contact with ultrasonic energy coupling material 380 contained in interior portion 551a and 551b of housing 551 to enhance the transmission and detection of ultrasound through wear face 554. Wear face 554 is in contact with a surface of sample S. Device 550 further includes ultrasonic energy absorbing material 386 extending along at least part of wall portion 558 of housing 551. Material 386 is so positioned to absorb ultrasound reflections from base 555 and echoes within device 550.

Figure 10:
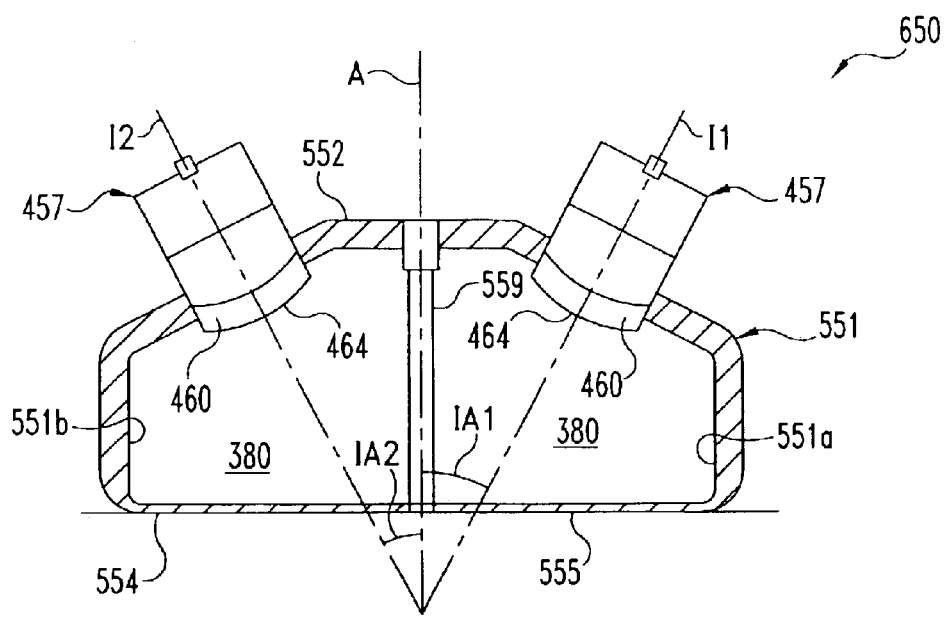
FIG. 10 is a partial diagrammatic side view of a fourth type of transducer device that can be included in the system of FIG. 1.

FIG. 10 schematically depicts dual element ultrasonic transducer device 650. Device 650 includes casing or housing 551 the same as that previously described in connection with FIGS. 8 and 9. Device 650 also includes two transducers 457 each as previously described in connection with device 450 of FIG. 7. In device 650, transducers 457 are both coupled to upper shell 552 in a fixed relationship opposite base 555. One of transducers 457 is oriented to direct its curved convex face 464 along axis I1 to form incident angle IA1 with axis A, and the other of transducers 457 is oriented to direct its curved convex face 464 along axis I2 to form incident angle IA2 with axis A. Angles IA1 and IA2 are generally equal and opposite one another about axis A. Element 460 of each transducer 457 is positioned inside interior 351a or 351b to direct the corresponding convex face 464 toward base 355 along axis I1 or I2, respectively. Elements 460 of each transducer 457 are each generally symmetric about the respective axes I1 and I2 which are each at an oblique angle with wear face 554 and axis A.

Convex face 464 of each element 460 is in contact with ultrasonic energy coupling material 380 contained in interior portion 551a and 551b of housing 551 to enhance the transmission and detection of ultrasound through wear face 554. Wear face 554 is in contact with a surface of sample S. Device 550 further includes ultrasonic energy absorbing material 386 extending along at least part of wall portion 558 of housing 551 as shown in FIG. 8. Material 386 is so positioned to absorb ultrasound reflections from base 555 and echoes within device 650.

In the case where smooth inspection surfaces are available, the diverging sound field can be focused at the surface of the part. Dual spherical elements such as those provided by devices 550 and 650 of FIGS. 8–10 frequently provide a low noise arrangement. The elements can be separated by an ultrasonic insulator (such as wall 559) to keep large excitation energy away for the receiving element. Nonetheless, in other embodiments having a rough surface, a dual element transducer device can still be used.

Figure 11:
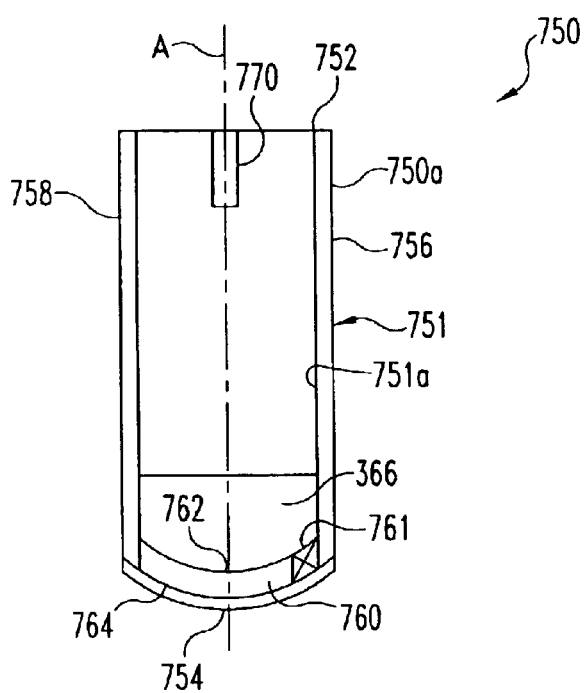
FIG. 11 is a partial diagrammatic side view of a fifth type of transducer device that can be included in the system of FIG. 1.

FIG. 11 schematically depicts transducer device 750. Device 750 is in the form of an immersion probe 750a, and includes housing 751 defining interior 751a. Housing 751 includes proximal portion 52 opposite distal base portion 755. Portion 755 defines curved wear face 754. Housing 751 also includes wall portion 756 opposite wall portion 758.

Device 750 includes active element 760 having a curved concave face 762 opposite a curved convex face 764, the same as described in connection with device 450 of FIG. 7 except that is includes a "deadened" inactive portion 761 to reduce echoing. In alternative embodiments more deadened portions are utilized or are absent. Element 760 is spaced apart from base 755 and is positioned inside interior 751a to direct convex face 764 toward wear face 354 along axis A. Element 760 is generally symmetric about axis A and can be circular, elliptical, rectangular or such other curvilinear and/or rectilinear shape. A backing material 366 is provided to at least partially fill interior 751a and device 750 includes connector 770 to which active element 760 is connected via appropriate cabling or wiring through interior 751a (not shown).

Figure 12:
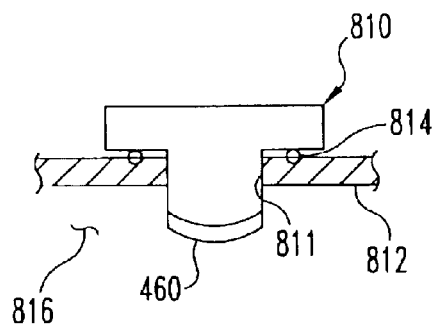
FIG. 12 is a partial diagrammatic side view of a sixth type of transducer device that can be included in the system of FIG. 1.
Figure 13:
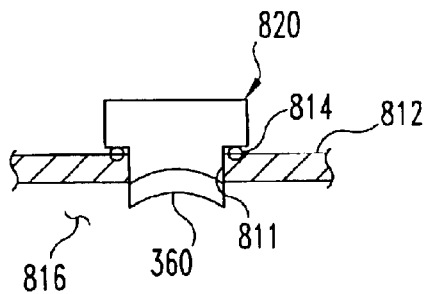
FIG. 13 is a partial diagrammatic side view of an seventh type of transducer device that can be included in the system of FIG. 1.

FIGS. 12 and 13 schematically depict screw-in transducer device 810 and 820, respectively. Devices 810 and 820 each include threads to engage threading defined by containment wall 812 about aperture 811. Devices 810 and 820 include seal 814 to engage wall 812 and provide secure containment of a beam forming material 816. Device 810 includes active element 460 in contact with material 816 when securely threaded through aperture 811 of wall 812. Active element 460 is the same as previously described in connection with FIG. 7. Device 820 includes active element 360 in contact with material 816 when securely threaded through wall 812. Active element 360 is the same as previously described in connection with FIG. 6. It should be appreciated that the threaded coupling of devices 810 and 820 can be used to insert and remove transducers 357 and/or 457 from various housings as described in connection with FIGS. 6–10.

Figure 14:
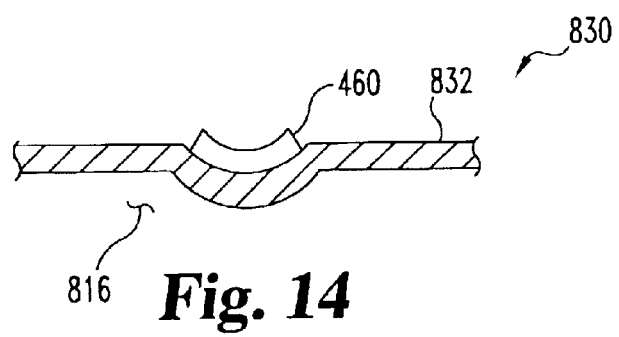
FIG. 14 is a partial diagrammatic side view of an eighth type of transducer device that can be included in the system of FIG. 1.
Figure 15:
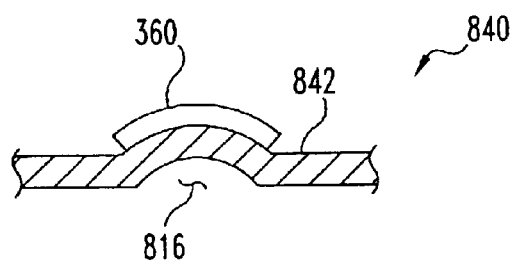
FIG. 15 is a partial diagrammatic side view of a ninth type of transducer device that can be included in the system of FIG. 1.

FIGS. 14 and 15 each schematically depict embedded active element applications. In FIG. 14, transducer device 830 includes active element 460 previously described in connection with FIG. 7. Element 460 is embedded to contact transfer layer 832 which in turn contacts beam forming material 816. In FIG. 15, transducer device 830 includes active element 360 previously described in connection with FIG. 6. Element 360 is embedded to contact transfer layer 842 which in turn contacts beam forming material 816.

It should be appreciated that many of the features of the transducer devices of FIGS. 6–15 can be interchanged, duplicated, and deleted in alternative embodiments. For example, one or more deadened portions can be incorporated into the active element of any of these devices. In another example, a curved active element has a shape other than a spherical concave or convex type. In yet another example, a curved ultrasound lens is utilized in place of a curved active element face. In still other examples, more or less backing material, absorbing material, coupling material, and the like may be utilized. It should be understood that elements 260, 360, 460, and 760 for any of the embodiments depicted in FIGS. 6–15 and variations thereof can be made from a piezoelectric material or such other material suitable for generating ultrasonic energy in response to electrical input and/or generating an electrical output in response to the detection of ultrasonic energy.

In most transducer applications of SAFT, resolution is generally no better than the resolving power of the transducer used. Other factors can further limit resolution. At 5.0 MegaHertz (MHz), an f2 transducer typically limits resolution to 0.5 mm and a similar f12 transducer typically limits resolution to 3.0 mm. The desire to insert significant acoustic power derives from the diverging beam for image reconstruction. Spherically shaped active elements can provide both low f-number and high acoustic power.

To demonstrate the relative performance of different types of ultrasonic transducers, Table 1 below shows the resolution performance for selected transducer types. The table includes a column for a design type. The "type" field specifies if the transducer has a flat element or gives an f-number if the transducer has a spherical element. The type field also states the transducer mount material as plastic or water. The frequency range under investigation for LR SAFT transducers is 2–10 MHz. The velocity and wavelengths for the sound in the transducer mount is given in the table because it affects the performance of the transducer. The diameter of the flat or spherical element is also given. The focal length is the radius of curvature of the spherical element. For spherical elements, the f-number is the focal length divided by the element diameter. Resolution is the quantity of interest with smaller numbers being more desirable. Resolution for flat element probes is estimated as half the diameter of the flat element. Resolution for spherical element probes is the wavelength in the wedge multiplied by f-number.

The performance factor in the table is the ratio of flat probe's resolution to the spherical probe's resolution.

TABLE 1

Performance for LR SAFT Transducers by Type

| Type | Freq. MHz | Velocity (mount) in/usec | wavelen. (mount) inches | Dia. (in.) | Focal Len. inches | f-number | Resolution −3 dB inches | Factor |
|---|---|---|---|---|---|---|---|---|
| Flat 2.0 MHz | 2 | (na) | (na) | 0.5 | (na) | (na) | 0.25 | 1.0 |
| F5 plastic | 2 | 0.108 | 0.054 | 0.75 | 4 | 5.3 | 0.29 | 0.9 |
| F5 water | 2 | 0.0548 | 0.027 | 0.75 | 4 | 5.3 | 0.15 | 1.7 |
| Flat 3.5 MHz | 3.5 | (na) | (na) | 0.5 | (na) | (na) | 0.25 | 1.0 |
| F4 plastic | 3.5 | 0.108 | 0.031 | 0.75 | 3 | 4.0 | 0.12 | 2.0 |
| F2 plastic | 3.5 | 0.108 | 0.031 | 0.75 | 1.5 | 2.0 | 0.06 | 4.1 |
| F8 water | 3.5 | 0.0548 | 0.016 | 0.75 | 6 | 8.0 | 0.13 | 2.0 |
| F4 water | 3.5 | 0.0548 | 0.016 | 0.75 | 3 | 4.0 | 0.06 | 4.0 |
| F2 water | 3.5 | 0.0548 | 0.016 | 0.75 | 1.5 | 2.0 | 0.03 | 8.0 |
| Flat 5 MHz | 5 | (na) | (na) | 0.25 | (na) | (na) | 0.13 | 1.0 |
| F8 water | 5 | 0.0548 | 0.01096 | 0.5 | 4 | 8.0 | 0.09 | 1.4 |
| F4 water | 5 | 0.0548 | 0.01096 | 0.5 | 2 | 4.0 | 0.04 | 2.9 |
| F2 water | 5 | 0.0548 | 0.01096 | 0.5 | 1 | 2.0 | 0.02 | 5.7 |
| Flat 10 MHz | 10 | (na) | (na) | 0.25 | (na) | (na) | 0.13 | 1.0 |
| F8 water | 10 | 0.0548 | 0.00548 | 0.5 | 4 | 8.0 | 0.04 | 2.9 |
| F4 water | 10 | 0.0548 | 0.00548 | 0.5 | 2 | 4.0 | 0.02 | 5.7 |
| F2 water | 10 | 0.0548 | 0.00548 | 0.5 | 1 | 2.0 | 0.01 | 11.4 |

The imaging performance of SAFT-UT transducers described in Table 1 was tested with a resolution standard and a sizing standard. The resolution standard was composed of 6 mm diameter flat bottom holes with hole spacing from 0.5 mm to 8 mm. Resolution can be estimated by imaging the remaining ligament between holes. The sizing standard used flat bottom holes with diameters between 1 mm and 8 mm. The sizing performance is evaluated by comparing −6 dB image size to the hole true state.

Figure 16:
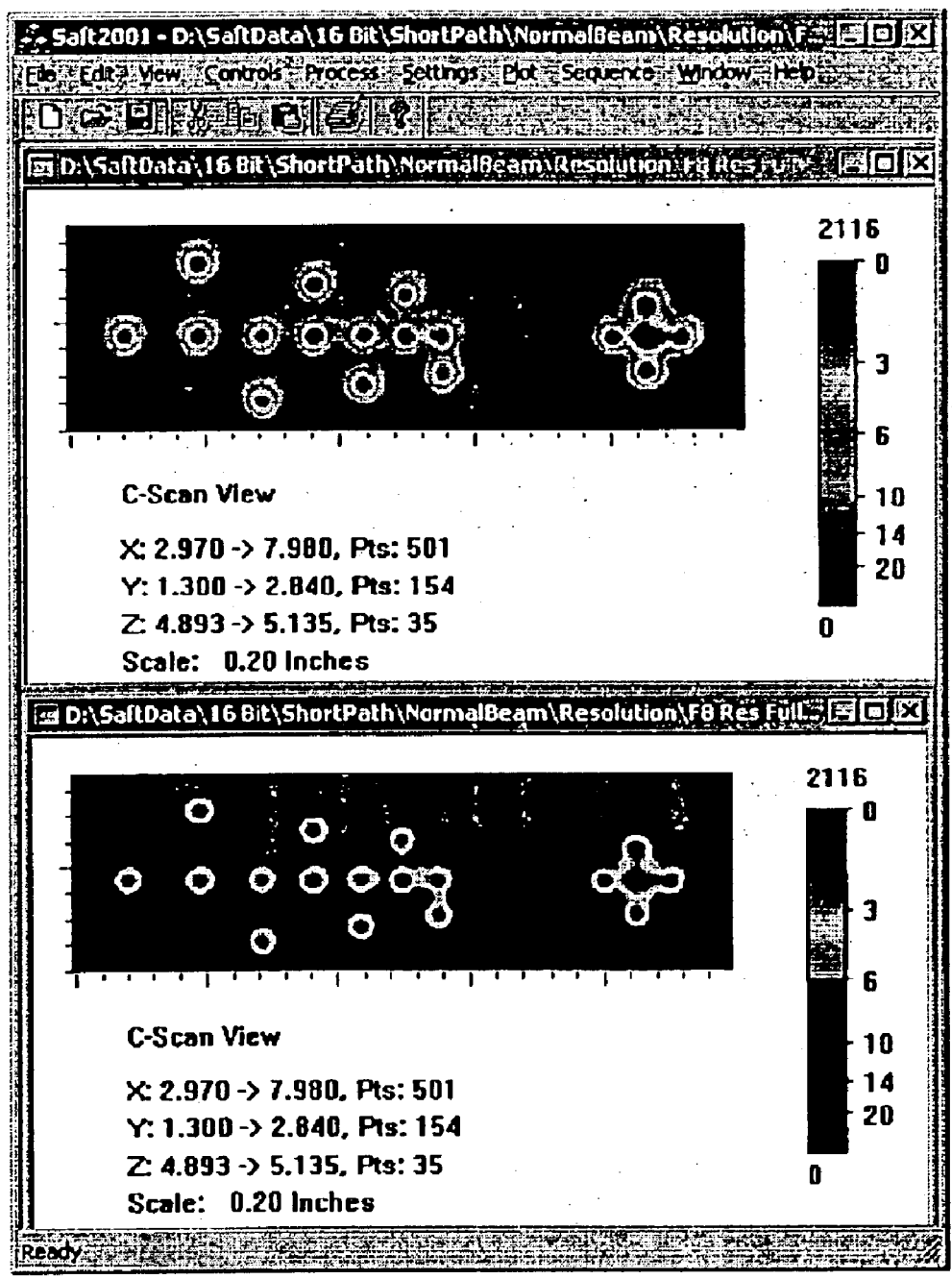
FIGS. 16–18 are computer-generated images of results from experimental testing of f8, f4, and f2 spherical ultrasonic transducer elements, respectively.

The resolution of using an f8 spherical element transducer is shown in FIG. 16. The resolution standard is composed of 6 mm diameter flat bottom holes. From left to right the hole separation is 8, 6, 4, 3, 2, 1 mm and 0.5, 0.5 mm. The lower image shows a −6 dB clip of the upper image. For this 10 MHz f8 element, the resolution is shown to be 1 mm at −3 dB and 2 mm at −6 dB.

The resolution using an f4 spherical element transducer is shown in FIG. 17. The resolution standard is composed of 6 mm diameter flat bottom holes. From left to right the hole separation is 8, 6, 4, 3, 2, 1 mm and 0.5, 0.5 mm. The lower image shows a −6 dB clip of the upper image. For this 10 MHz f2 element, the resolution is shown to be less than 0.5 mm at −3 dB and 0.5 mm at −6 dB.

Figure 18:
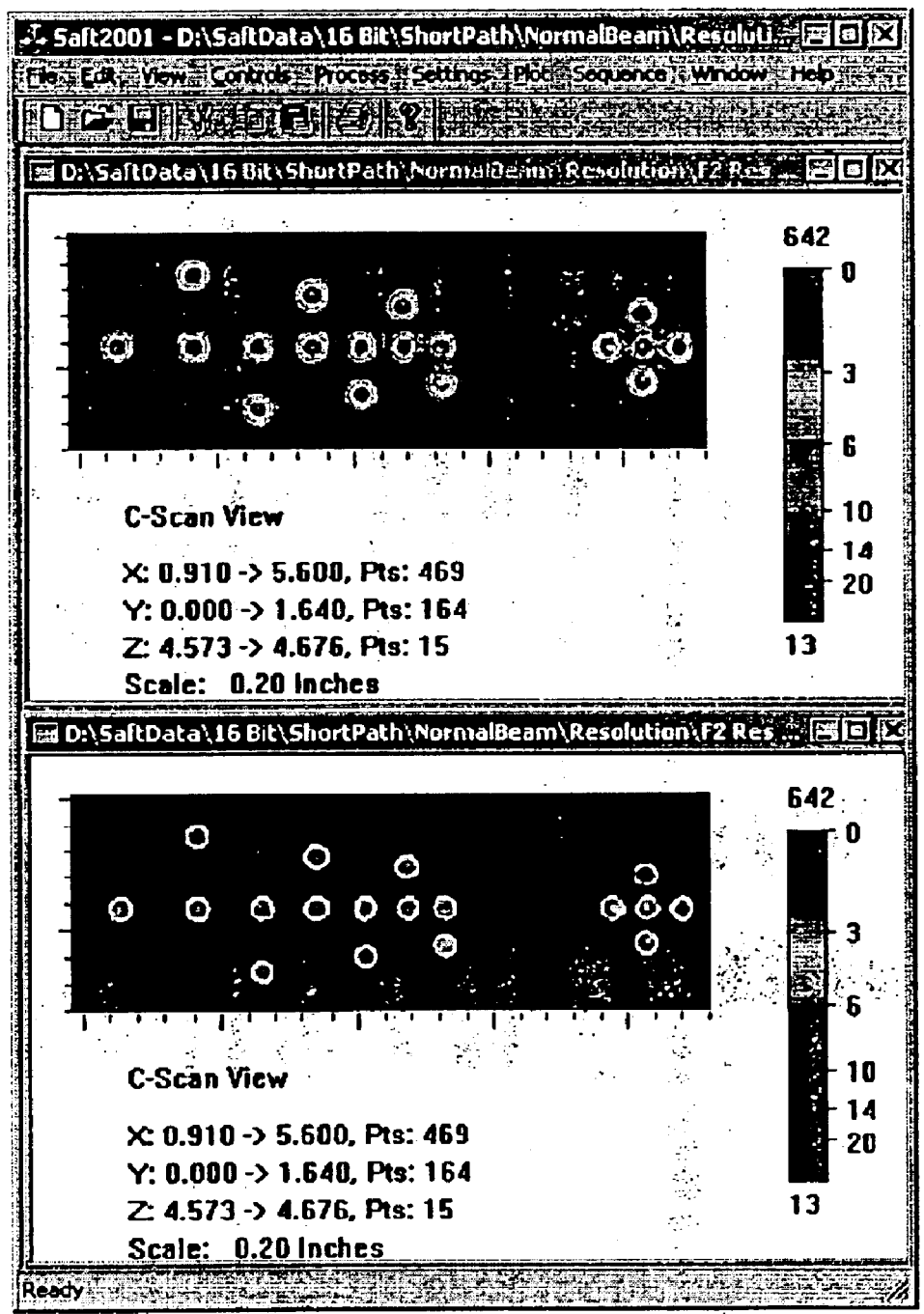

The resolution using an f2 spherical element transducer is shown in FIG. 18. The resolution standard is composed of 6 mm diameter flat bottom holes. From left to right the hole separation is 8, 6, 4, 3, 2, 1 mm and 0.5, 0.5 mm. The lower image shows a −6 dB clip of the upper image. For this 10 MHz f2 element, the resolution is shown to be less than 0.5 mm at −3 dB and 0.5 mm at −6 dB.

Figure 19:
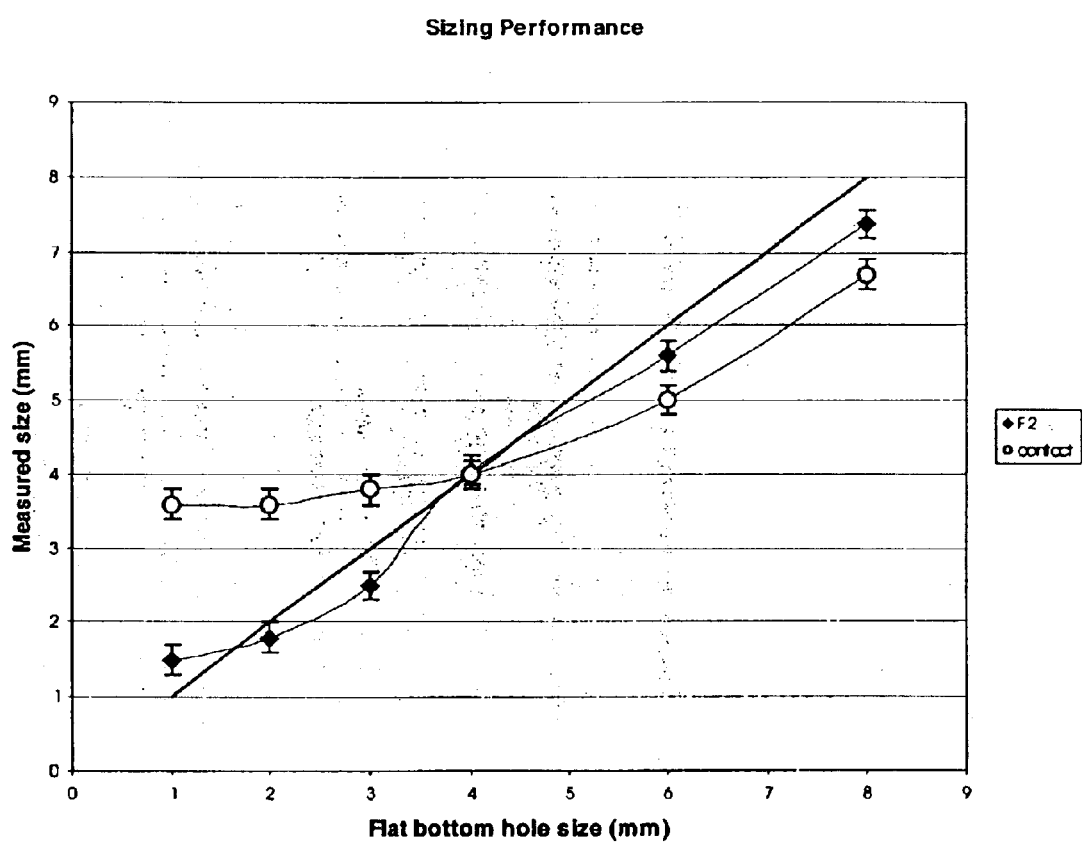
FIG. 19 is a comparative graph of sizing performance for two different ultrasonic transducers.

Sizing performance of the SAFT-UT system on flat bottom holes with diameters of 1, 2, 3, 4, 6, and 8 mm is shown in FIG. 19. Two ultrasonic transducers were used, a 6 mm diameter flat contract probe with a −6 dB resolution of 3.5 mm and an f2 spherical element with a −6 dB resolution of 0.5 mm.

Table 2 below gives the elementary properties, such as center frequency, for five convex prototypes and five concave prototypes. The frequency and beam forming medium is kept constant for these prototypes. F-numbers range from 2 to 8.3. For three of the five prototypes, the element diameter is held constant, at 12 mm, to test the performance with varying focal length. For three of the prototypes, the focal length is held constant to test the performance with varying element diameter. Expected resolution is given in the table.

TABLE 2

Elementary Properties for Concave and Convex Prototypes

| ID | Frequency (MHz) | Beam forming medium | f# | Element diameter (mm) | Focal Length (mm) | Resolution (mm) |
|---|---|---|---|---|---|---|
| #1 | 10 | water | 2 | 12 | 25 | 0.37 |
| #2 | 10 | water | 4 | 12 | 50 | 0.76 |
| #3 | 10 | water | 8 | 12 | 100 | 1.5 |
| #4 | 10 | water | 2.6 | 19 | 50 | 0.49 |
| #5 | 10 | water | 8.3 | 6 | 50 | 1.6 |

A device with a convex spherical active element face for full volume focusing of the type shown in FIG. 7 has been prototyped with the following results. Corresponding assemblies featured threaded transducer mounts, separate transducer mounts for insonification angles of 0 and 70 degrees, and transducers with coaxial connectors in 1.0" diameter cases. The center frequency was 2.0 MHz and the bandwidth is 40% at the minus 6 dB points of the power spectrum. The active elements are 0.75" inches in diameter with a spherical radius of 4.0".

Among the applications of the various inventions disclosure herein is Non-Destructive Evaluation (NDE). NDE is an industrial science pertinent to medicine, defense, and other areas. Industrial application of NDE is often part of internal quality assurance programs for metals, components, and systems. The industrial inspection environment determines much of the NDE technology that must be deployed.

The large metal components and systems used in energy production and industrial energy consumption are significant investments that require maintenance and safety assessments. For this reason, reliable detection and accurate characterization of flaws and degradation in these systems can have significant value.

The purpose of the industrial application of NDE is to detect degradation in time so that corrective action can be taken before the degradation challenges the structural integrity of the system or its components. Accurate characterization is required to distinguish progressive degradation from benign conditions. In NDE, characterization includes quantification and description of location, dimensions, shape, orientation, and composition of a flaw or other condition. An imaging system that uses SAFT is one choice for ultrasonic characterization of degradation in metals, components, systems, and structures.

In one particular example, a Synthetic Aperture Focusing Technique for Ultrasonic Testing (SAFT-UT) in accordance with the teachings of the present application can be used for characterization of fabrication flaws in nuclear reactor pressure vessels. Recent ultrasonic measurements of fabrication flaws, especially those associated with repairs, are given. Image quality from the inspection of RPV material is explained including the imaging of weld microstructure. Distinguishing fabrication flaws from microstructural conditions requires significant dynamic range and knowledge of the characteristics of the weld microstructure. The development of this imaging capability is a key element for the characterization of RPV flaws.

A SAFT-UT inspection system comparable to system 20 was used for building research quality data sets on fabrication flaws. In SAFT-UT, the focal properties of a large focused transducer are generated by digital signal processing of data collected over a large area using a small transducer with a diverging sound field. SAFT has an advantage over physical focusing techniques in that the resulting image is full-volume focused over the entire inspection area. Traditional physical focusing techniques provide focused images only over a limited zone at the depth of focus of the lens. A second benefit in SAFT processing is that the coherent summation for each image point involves shifting a locus of A-scans, within a regional aperture, by predicting time delays and summing the shifted A-scans. Each picture element is then a spatial average producing an enhanced signal-to-noise performance suitable for detection and characterization of small reflectors in heavy-section steel. Accurate characterization of the flaws in the RPVs required separate density and distribution estimates according to product form. RPV construction records can be used to estimate product form volumes and other characteristics for specific vessels. The methodology for extending flaw density and distribution by product form to a generalized flaw distribution is given in Jackson D A, Abramson L, Doctor S R, Simonen F A, and Schuster G J, "Development of a Generalized Flaw Distribution as Input to the Re-evaluation of the Technical Basis for U.S. Pressurized Thermal Shock Regulation of Water Reactor Vessels," $3^{rd}$ International Conference on NDE in Relation to Structural Integrity for Nuclear and Pressurized Components, Nov. 14–16, 2001, Seville, Spain. 2001.

SAFT-UT inspections of RPV samples used weld-normal testing to produce flaw density distributions by product form. Product forms included machine-made weld, manual-applied weld, weld applied in repair cavities, etc. Images are presented of indications of flaws found in the various product forms. Images are also provided showing how the presence of repair cavities can be detected.

Figure 20:
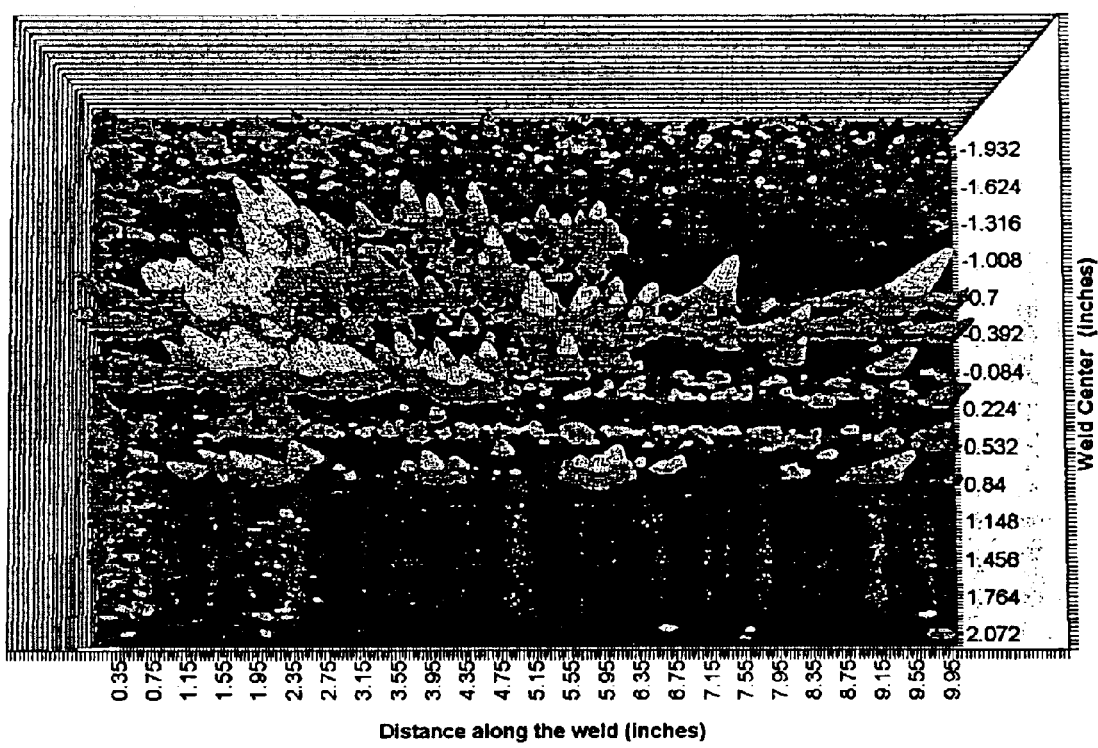
FIGS. 20–24 are computer-generated images of experimental results relating to the inspection of welds.

FIG. 20 shows the image used to detect the repair and estimate dimensions for the product form using through-wall cross section (circumferential profile) generated by the fusion surface of the repair. The image can be subdivided into regions of distinct product form, base metal (two regions), submerged arc weld (SAW) weld metal, and repair metal.

The repair was made to the fusion line of the weld with the upper region of base metal. The repair's dimensions can be read from the axis labels as approximately 4 inches (10 cm) along the weld and 1.5 inches (37 mm) across the weld. The repair area shown is approximately elliptical as expected for a through-wall cross section. The repair end, on the left, shows the strongest responses. These responses range from −22 dB to −42 dB with respect to a 0 dB calibration response. The repair's extremities, used to detect and estimate product form volumes, are evidenced by the ultrasonic responses from the flaws on the repair's fusion surfaces with the base metal and the weld. The flaw characterization, especially for the responses on the left end of this repair, is reported in Doctor S R, Schuster G J, Kietzman E, and Rassler B, "Destructive Validation Methodology and Results for the Characterization of Flaws in Nuclear Reactor Pressure Vessels," $3^{rd}$ International Conference on NDE in Relation to Structural Integrity for Nuclear and Pressurized Components, Nov. 14–16, 2001, Seville, Spain, 2001.

The SAW weld, joining the two base metal regions, runs horizontally in the image. The distance across the weld can be read for the vertical axis labels as ±0.7 inches (±18 mm). The scale used on the vertical axis is distance from weld centerline. The weld's profile in this case was straight wall and the simple shape contributed to alignment of the fusion lines at ±0.7 inches. The strongest responses from the SAW originate with the flaws on the weld's fusion lines with the two base metal regions. The lines run horizontally in the image. The responses from the fusion lines, in this case, vary between −22 dB and −52 dB with respect to the calibration response. The microstructural responses, from the long-axis grains in the SAW, are apparent in the image. These responses, in three horizontal bands, identify the SAW product form. The bands contain weak responses between −54 dB and −58 dB.

Figure 21:
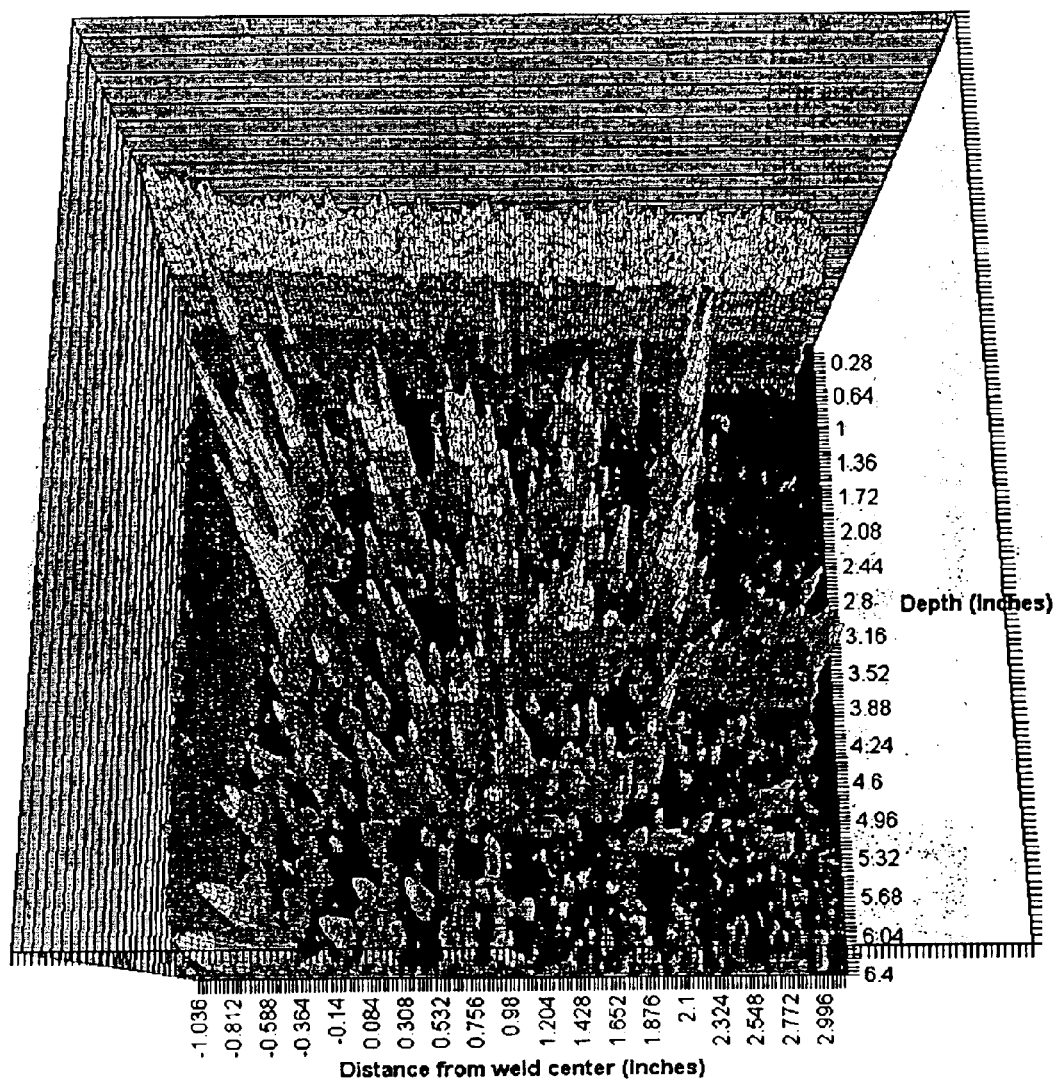

FIG. 21 shows the detection and circumferential cross section (through-wall profile) of a second weld repair in a weld from a nuclear reactor pressure vessel. The image has five product form regions, cladding, repair, SAW metal, and two base metal regions. The repair was made to the fusion line of the weld with the region of base metal on the right. The repair was made from the vessel's inside surface to a depth of approximately 5 inches (12 cm). The width of the repair, across the weld, can be read from the horizontal axis as approximately 3 inches (7.5 cm). The shape is approximately parabolic as expected for an axial cross section. This cross section shows the side of the repair rather than the ends as seen in the previous figure. The responses on the side of the repair range from −10 dB to −50 dB.

The SAW, joining the two base metal regions, runs vertically in the image. The distance across the weld is approximately ±0.8 inches (20 mm). Approximately 1.5 to 2.0 inches of the bottom portion of the weld has not been removed by the repair. The strongest responses from the weld can be found on the fusion line with the left portion of the base metal. Microstructural responses, from the long axis grains of the SAW, are apparent in the image. These responses form three vertical bands of weak responses between −48 dB and −52 dB.

A base metal flaw is apparent in the image at a depth location of 3.5 inches (9 cm), approximately mid-wall for the BWR plate material. The cladding is shown as a high response line, −26 db, starting at 0.25 inches (6 mm) of depth.

Figure 22:
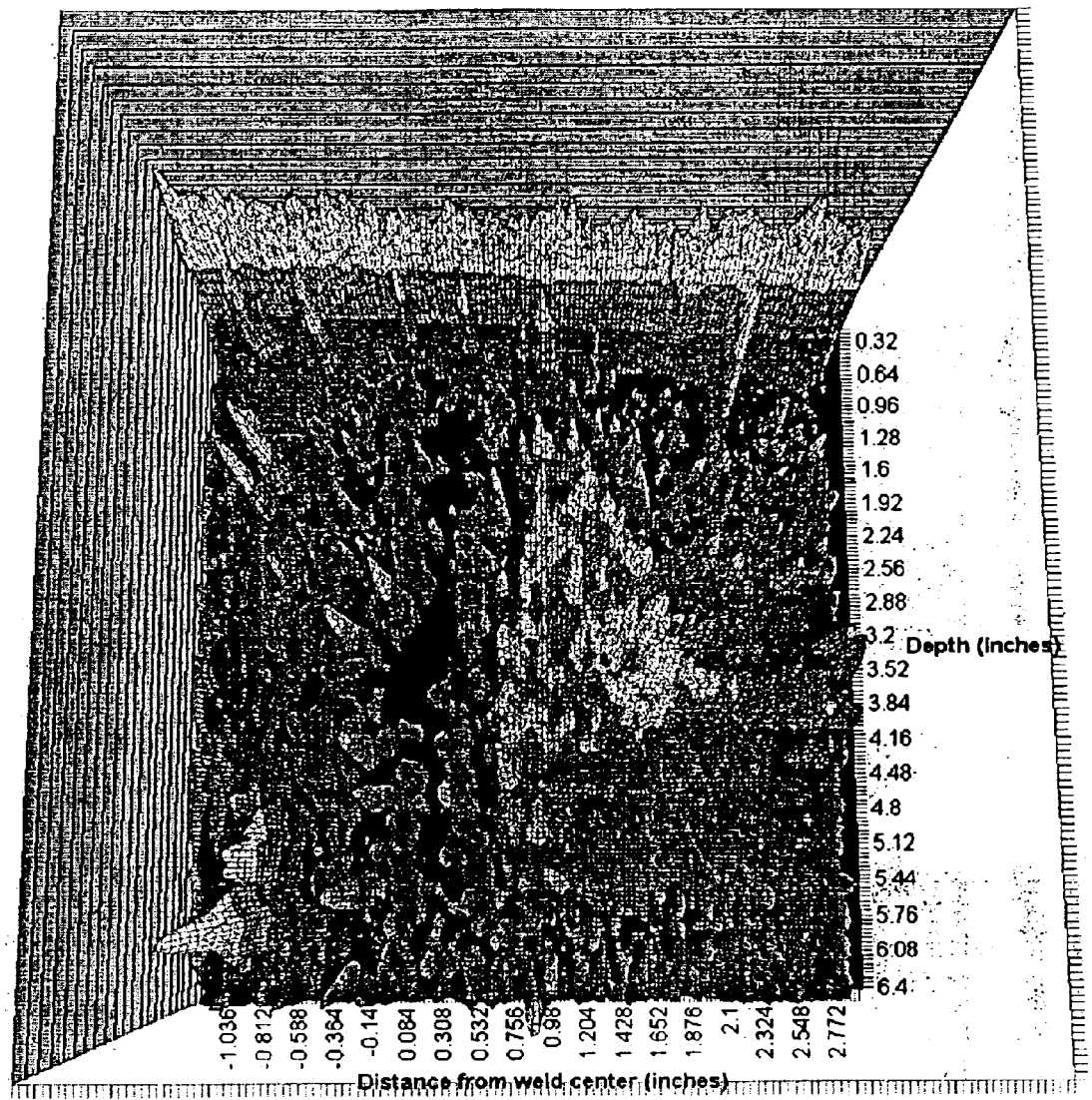

FIG. 22 shows the detection and circumferential cross section (through-wall profile) of a repair to the base metal's weld preparation surface. The image can be subdivided into five regions, cladding, repair, SAW, and two base metal regions. The repair was made to base metal plate. After the plate was prepared for welding, a flaw in the plate was detected by magnetic particle testing. The flaw was removed for a distance of approximately 0.8 inch (2 cm) into the base metal plate and then the cavity was filled with weld metal. The repair's depth dimension can be read from the axis labels as 4 inches (10 cm) in the depth direction. The shape of the repair is approximately that of a part circle, truncated by the fusion line of the SAW. The strongest responses from the repair are on the fusion surface with the SAW and with the base metal. The responses are distribution between −22 dB and −42 dB.

A flaw can be seen extending from the base metal repair into the base metal at a depth location of approximately 3.5 inches (9 cm). This mid-wall flaw is a remaining portion of the flaw that was detected and removed to prepare the plate for welding.

Figure 23:
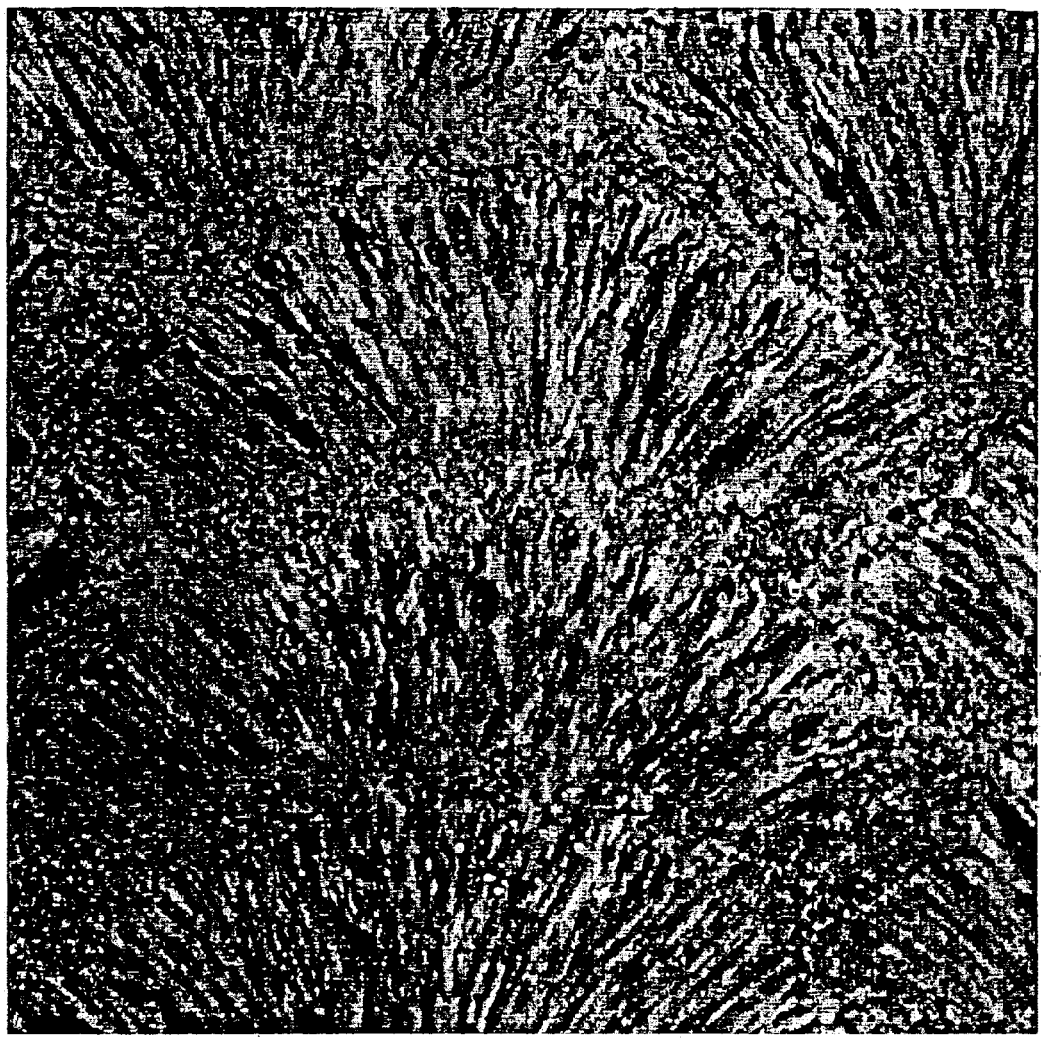

The coarser-grained weld microstructure in machine made-weld passes consistently produces identifiable responses in the weld-normal inspections. The SAFT-UT images show that these responses originate within the weld-beads where the grain structure is most favorably oriented to return acoustic energy. The images of weld microstructure can be used to distinguish SAW product from SAW. FIG. 23 shows a micro-polish and etch of SAW passes from the machine-made portion of a weld in a nuclear reactor pressure vessel. There are two types of distinct microstructure in SAW, long axis grains and equal axis grains. The microstructure forms into regions traceable to the weld passes that were used to construct the weld.

The weld passes are shown as an axial cross section with the depth axis oriented vertically in the figure. The location of these weld passes are at approximately 6 inches of depth and on the weld centerline. The long axis grains form a region that is approximately 0.5 inch (12 mm) across the weld and 0.25 inch (6 mm) in depth. The equal axis grains border the long axis regions with a thickness of 0.1 inch (2.5 mm).

The regions of long axis grains are isolated from each other and have depth boundaries of constant radius and with boundaries of constant polar angle. The equal axis microstructure forms one continuous region, zig-zagging vertically between the weld passes and following the radius of curvature of the long axis regions across the weld.

Figure 24:
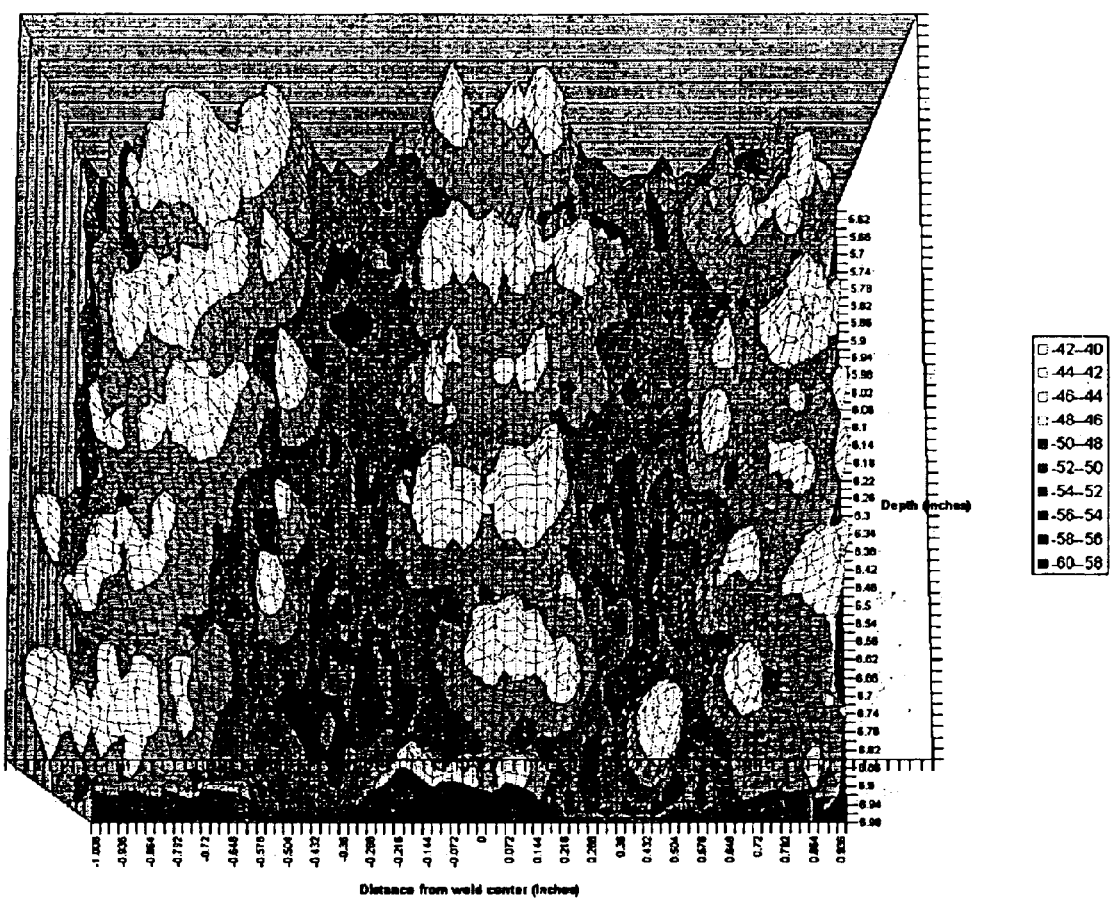

Five regions of microstructural responses are shown in FIG. 24, three columns of relatively bright responses from regions of long axis grains and two columns of low response from equal axis grains. The vertical axis shows the depth location and horizontal axis shows the location of the responses with respect to weld center. The width of the low response columns is 0.4 inches (10 mm) where −54 dB is used for the measurement. This width is larger than the 0.1-inch (2.5 mm) width of the equal axis regions. One explanation for the discrepancy is the change in response that is expected between the long axis grains that are favorably oriented to the weld normal SAFT-UT, those at the center of their region, and those that are not so favorably oriented. Vertical separation between regions of response from the long axis grains can be seen at a higher response threshold of −50 dB. The 3.5-mm SAFT-UT resolution for this image is one source of energy that can smear the image in the vertical axis.

The objective of this work is to provide validation data on the characteristics of the flaws in the RPV vessels for use in fracture mechanics calculations. An approach was selected that produced high-resolution, up to 0.5 mm, ultrasonic images of the larger flaws, found in weld repairs. A description of the technique that was developed and used to construct the high-resolution images of the larger flaws is provided. The section concludes with a discussion of future work on SAFT reconstruction using current computing technology. This section reports the laboratory measurements that show the resolution and sizing performance that was obtained for validated measurements of fabrication flaw dimensions. The technique used more optimally shaped ultrasonic elements to achieve the needed imaging performance. The performance features selected for the SAFT transducers affected resolution, acoustic power, coupling, and signal to noise. Measurements of resolution and sizing error are given in this section.

The SAFT imaging system's lateral resolution is determined by the maximum of two separate resolution elements, the transducer's and the synthetic aperture's. In most applications of SAFT-UT, the system resolution will be no better than the resolving power of the transducer that is used. Other factors can limit the system resolution but a 5.0-MHz 6-mm diameter contact probe limits the system resolution to 3.5 mm. For spherical elements, the transducer's lateral resolution, $\bigcirc X_t$, is given by equation (a) as follows $$\bigcirc X_t = 1.22 \cdot f_L / A_t \tag{a}$$

where $\lambda_c$=wavelength in the coupling material, $f_L$=focal length of the transducer, and $A_t$=transducer aperture.

The synthetic aperture's lateral resolution, $\bigcirc X_s$, is given by equation (b) as follows $$\bigcirc X_s = \lambda_m / 4 \tan\_\_ \tag{b}$$

where $\lambda_m$=wavelength in the metal, and

\_\_=SAFT aperture angle.

Figure 25:
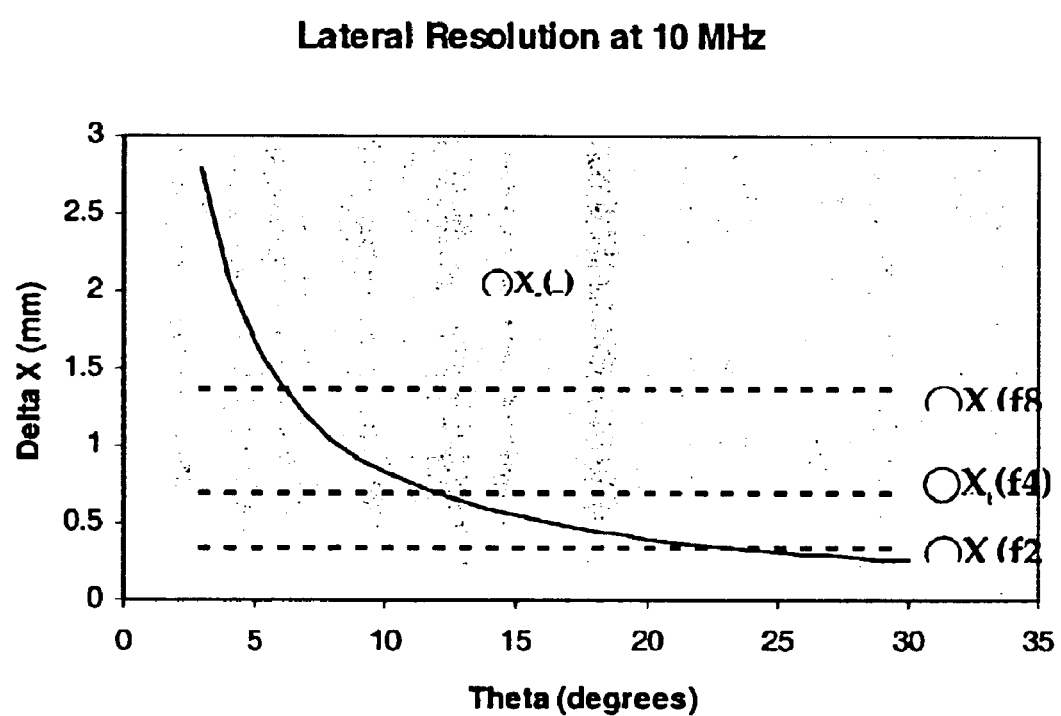
FIG. 25 is a comparative graph relating to SAFT resolution.

FIG. 25 is a graph of the theoretical lateral resolution for SAFT-UT images of reflectors in RPV steel using 10 MHz spherical elements. The graph shows the synthetic aperture resolution and probe resolution vs. the aperture angle. The optimum resolution and processing angle for the SAFT-UT images can be found at the intersection of $\bigcirc X_t$ and $\bigcirc X_s$.

Table 3 shows the resolution performance for selected transducer types. The table includes a column for a design type. The type field specifies the transducer frequency and standoff material. For this study, contact probes have flat elements and immersion probes have spherical elements. The frequency selected for the validation and characterization of the large flaws was 10 MHz. The wavelength for the sound in the transducer standoff is given in the table because it affects the resolution performance as given in Equation (a). The diameter of the flat or spherical element is given. The focal length is the radius of curvature of the spherical element. For spherical elements, the f-number is the focal length divided by the element diameter. Resolution is the quantity of interest with smaller numbers being more desirable. Resolution for flat element probes is estimated as half the diameter of the flat element.

For SAFT, the ultrasonic beam must diverge so that the reconstruction can find time-of-flight shapes associated with acoustic anomalies. The SAFT transducers used in the previous weld-normal inspections were small 6-mm diameter contact probes. These probes are low-power devices that limit the resolving power of SAFT, but are very robust for inspecting large blocks of RPV material.

A requirement for the insertion of significant acoustic power derives from the diverging beam requirement for image reconstruction. Spherically shaped active elements provided both low f-number and high acoustic power. The results reported here used 12-mm spherical elements.

TABLE 3

Performance for SAFT Transducers by Type

| Type | $\cdot c$ (mm) | $A_t$ (mm) | $f_L$ (mm) | f-number | Resolution −3 dB (mm) |
|---|---|---|---|---|---|
| 5 MHz Contact | n/a | 6.4 | n/a | n/a | 3.2 |
| 10 MHz Immersion | 0.139 | 12.7 | 102 | 8.0 | 1.36 |
| 10 MHz Immersion | 0.139 | 12.7 | 50.8 | 4.0 | 0.68 |
| 10 MHz Immersion | 0.139 | 12.7 | 25.4 | 2.0 | 0.34 |

Spherically shaped ultrasonic elements are typically used to provide sound fields with intense, focused energy within a short focal distance. In SAFT applications, the difficulty with the spherical elements is that the acoustic energy reverberates inside the probe and inside the coupling material, contributing more to the received energy than some of the desired signals from the test component. A low-noise requirement can be stated that the energy from sound field noise sources be less than the baseline of part noise received from the test material. This requirement limited the usefulness of the initial probe design and a recommendation is made to look at technologies that reduce this systematic noise.

The imaging performance of SAFT-UT transducers described in Table 4 was tested with a resolution standard and a sizing standard. The resolution standard was composed of 6-mm diameter flat bottom holes with holes spaced from 0.5 mm to 8 mm. Resolution can be estimated by imaging the remaining ligament between holes. The sizing standard used flat bottom holes with diameters between 1 mm and 8 mm. The sizing performance is evaluated by comparing −6 dB image size to the hole's machined diameter.

Figure 26:
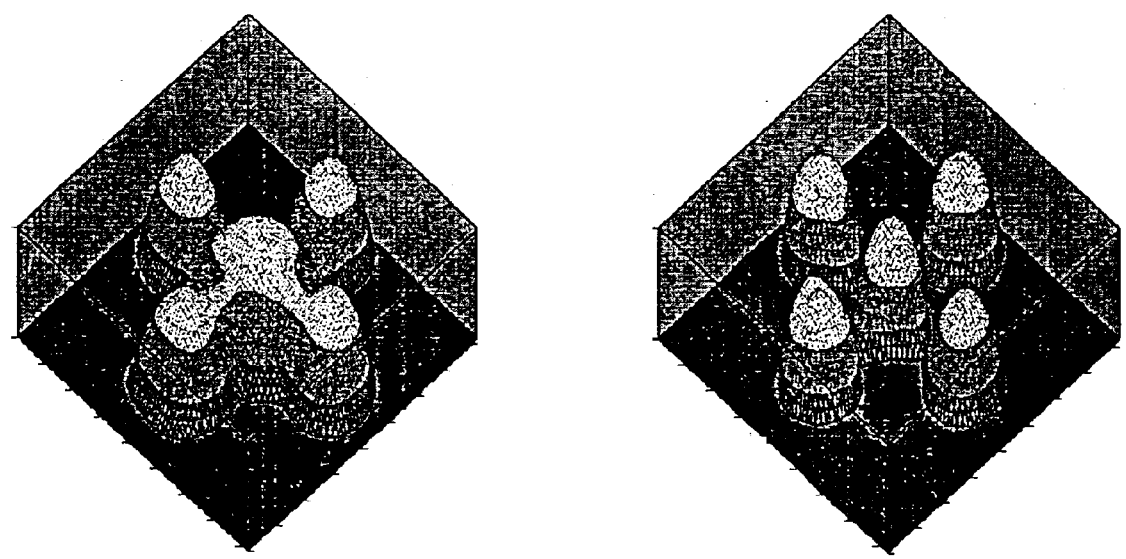
FIG. 26 present computer-generated images of experimental results comparing F8 and F2 spherical elements, respectively, for ultrasonic transducers.

Resolution of the SAFT-UT system using f8 and f2 spherical element transducers is shown in FIG. 26. The resolution standard is composed of five 6-mm diameter flat bottom holes separated by 0.5 mm (0.02 inch). For the 10-MHz f8 element shown on the left, the resolution element is shown to be greater than 0.5 mm at −3 dB. For the 10-MHz f4 element (not shown), the resolution was found to be 0.5 mm at −3 dB. For the 10-MHz f2 element shown on the right, the resolution is shown to be 0.5 mm at −6 dB. 8. The vertical axis shows 9 dB of total response change between the peak and the floor of these 3D contour plots. The two horizontal axis are 20 mm on a side. In the case of f8 probe, the responses from the holes are joined at the −2 dB level. In the case of the f2 probe, the responses are joined at the −8 dB level.

Sizing performance of the SAFT-UT system on flat bottom holes with diameters of 1, 2, 3, 4, 6, and 8 mm is shown in FIG. 19 as previously discussed. Two ultrasonic transducers were shown, a 6-mm diameter flat contract probe with a −6 dB resolution of 3.2 mm and an f2 spherical element with a −3 dB resolution of 0.34 mm.

The time to complete a SAFT reconstruction has historically limited application of the technology. This section describes the recent tests of coherent summation rate for SAFT algorithms and the expected performance that can be achieved with current computing technology. Use of computer algorithms that are designed for specific CPU architectures will produce reconstruction rates between 1–10 summations per CPU clock cycle.

The desired result for SAFT algorithm performance is near real-time behavior. Near real-time is defined as the completion of the focusing in the same amount of time as that needed to acquire the data. For material characterization, useful amounts of data can be acquired in $10^3$ seconds. Algorithms capable of $10^{10}$ summations per second per CPU can achieve near real performance for SAFT reconstruction as described below.

A simple test was conducted to evaluate the performance of coherent summation algorithms on modern CPUs. Here we have simplified the hyperbolic surface summation performed in SAFT to the simple case of summation on a plane. A further simplification is to sum all of the volume elements in each plane to the volume elements in that plane rather than restricting the summation to a circular aperture.

The first algorithm, called each volume element, mimics the behavior for the existing algorithm used in the SAFT-UT imaging system. This algorithm loops through the elements in the volume and adds the elements in the summation plane. The simple computation completes each volume element's summation before going on to the next volume element. The address change for each summation is of size n for this algorithm, where n is the number of depth samples. A second algorithm, called by vector, loops over the surface of the data volume adding depth vectors in the data volume. The same numerical result is achieved as in the each volume element algorithm but the address change is of size 2 for each summation. One address change is needed for the sum and one for the addend.

Figure 27:
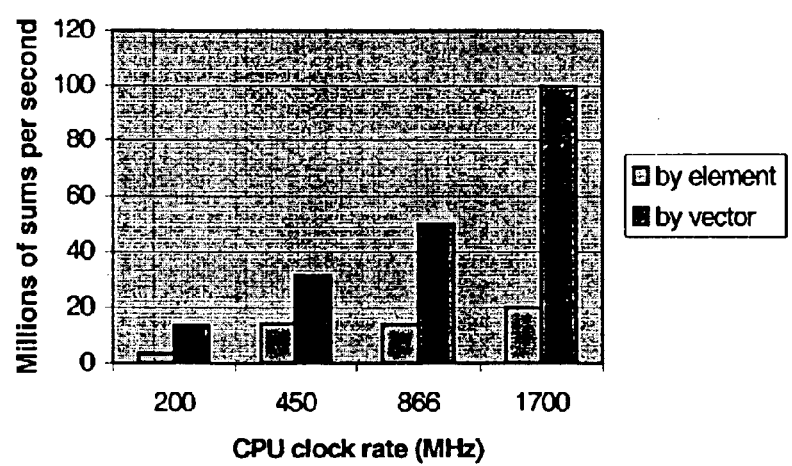
FIG. 27 is a comparative graph of two different SAFT processing routines in terms of CPU clock rate.

Two algorithms were quickly implemented and evaluated on four CPUs in the laboratory. The results of the tests are shown in FIG. 27. The summation rate for the by element algorithm did not scale with CPU speed. Data show that the execution has a high cache miss fraction of nearly 1.0. The CPU's memory cache provides data to the CPU at the CPU's clock rate provided that the algorithm's implementation does not generate high cache miss fraction. The performance penalty for a cache miss can be 20 CPU cycles or more so that the by element algorithm's performance does not scale with RAM access speed much less CPU clock rate. New SAFT algorithms should be designed to minimize address space change giving low cache miss fractions. The expected performance, using current computing technology, is a summation rate that is 1–10 times the CPU's clock rate.

An algorithm was designed that gave a summation rate of 1.3 times the CPU clock rate. Furthermore, the algorithm scaled with multiple CPUs with an efficiency of 98%. This was accomplished by stating the general computing problem, and constraining the solution with a computing model that uses the modern CPU features.

The Synthetic Aperture Focusing problem can be stated as the summation on a hyperbolic surface in a sampled volume for all points in that sampled volume. If the sampled volume is cubic with n samples on a side, then the order of magnitude of the general problem is $n^5$. SAFT inspections can generate data volumes with $10^9$ total volume elements, i.e., cubes with one thousand samples on a side. If worst-case complexity is assumed, then $10^{15}$ summations must be performed.

At present, the SAFT algorithm uses a look-up table of offsets to fetch values from off-center A-scans for the coherent summation. Significant improvements have been made in a new surface-following summation algorithm through the use of vector summations and synthetic aperture sampling. The summation rate has been shown to exceed the CPU clock rate using CPUs that perform an arithmetic instruction every clock cycle.

A second approach to optimizing the focusing algorithm is to sample the aperture across its entire diameter while skipping half or more of the data in it. Research shows that much of the summation can be skipped. Since it is the diameter of the synthetic aperture that determines the image resolution, we expect minimal changes in it. The scanning is still performed on half-wavelength steps but not all points in the aperture are accumulated in the coherent summation. Each step in the scan can be focused, giving a resultant image with half wavelength spacing. This new aperture sampling logic should replace the existing amplitude-based skip logic that permitted most of the inspection volume to go unprocessed.

A computation model is useful for designing high performance SAFT reconstruction algorithms. Table 4 below lists the features of interest with estimates of data transfer and summation rates. The data rate from disk is riot summation-rate-limiting provided that enough RAM is available to transfer the data once. Minimizing the total data transfer from RAM is a principle objective of the algorithm design. The data transferred from the L2 cache should all be useable by the CPU. The instruction pairing and use of vector registers is accomplished by design with instructions that are intrinsic to the specific target CPU.

TABLE 4

Modern CPU Features that are Relevant to SAFT Reconstruction

| CPU Feature | Data and Summation Bandwidth |
| --- | --- |
| Data rate from disk | 0.02 bytes per CPU clock cycle |
| Data rate from RAM | 0.2 bytes per clock cycle |
| Data rate from L2 cache | 32 bytes per clock cycle |
| Instruction execution | 2–8 instructions per clock cycle |
| Vector registers | 1–8 values per summation cycle |
| Target Coherent Sum Rate | 1–10 per clock cycle per CPU |

Figure 28:
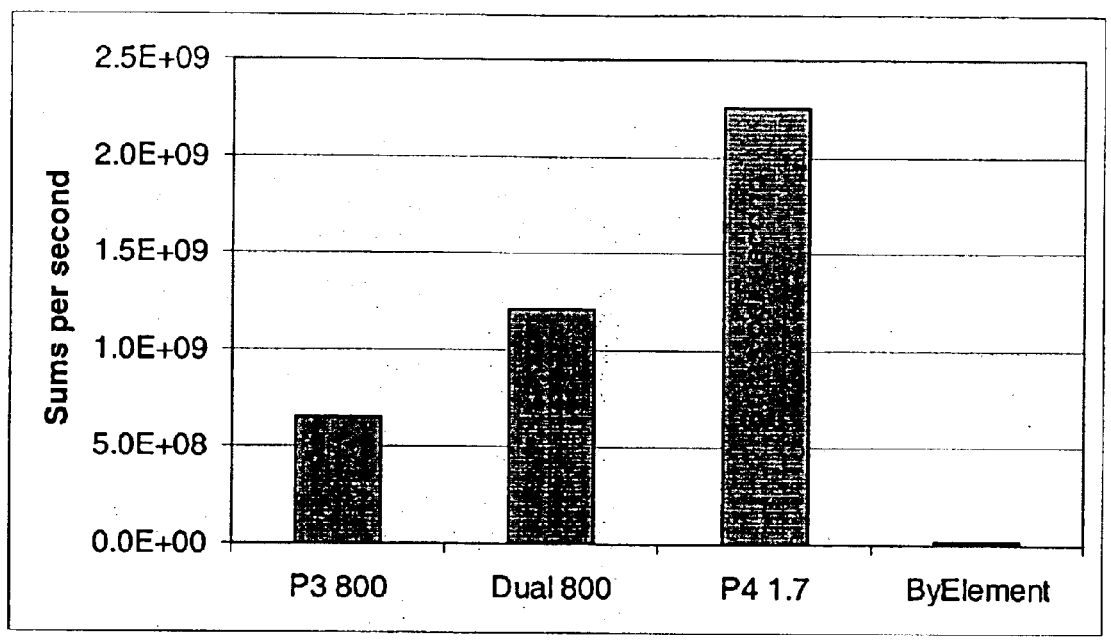
FIG. 28 is a comparative graph of a "by cross section" routine for several different CPU arrangements and a "by element" algorithm.

FIG. 28 shows a graph comparing the performance of the "by cross-section" technique on a planar surface. Two different CPUs were tested. A computer with dual CPUs was also utilized. The performance of the "by element" procedure is shown for comparison.

All publications, patents, and patent applications cited in this specification are herein incorporated by reference as if each individual publication, patent, or patent application were specifically and individually indicated to be incorporated by reference and set forth in its entirety herein. Further, any theory, mechanism of operation, proof, or finding stated herein is meant to further enhance understanding of the present invention and is not intended to make the present invention in any way dependent upon such theory, mechanism of operation, proof, experimental result, or finding. Further, any experimental results are intended to be examples to enhance understanding of the inventions of the present application and should not be limiting. While the invention has been illustrated and described in detail in the drawings and foregoing description, the same is to be considered as illustrative and not restrictive in character, it being understood that only selected embodiments have been shown and described and that all changes, modifications and equivalents that come within the spirit of the invention as defined herein and/or by the following claims are desired to be protected.

What is claimed is:

1. A method, comprising:

interrogating a sample with ultrasound;

generating data corresponding to ultrasonic energy returned by a volume of the sample in response to said interrogating;

performing a synthetic aperture focusing technique with the data including:

defining a number of hyperbolic surfaces extending through the volume at different depths and a corresponding number of multiple element accumulation vectors;

executing one focused element calculation procedure for a group of the vectors representative of an interior of a designated aperture;

executing another focused element calculation procedure for vectors corresponding to a boundary of the aperture; and providing an image corresponding to a feature of the sample in accordance with the synthetic aperture focusing technique.

2. The method of claim 1, wherein said interrogating is performed with a transducer device including two active elements each having a concave or convex face.

3. The method of claim 1, wherein said interrogating is performed with a transducer device including an active element with a curved face spaced apart from and directed toward a base of the device, the face being symmetric about an axis that intersects a plane coextensive with the base at an oblique angle, and which includes providing an ultrasound energy beam along the axis.

4. An apparatus, comprising: a device carrying logic executable by one or more processors to: (a) define a number hyperbolic surfaces extending through an ultrasonic interrogation sample volume at different depths and a corresponding number of multiple element accumulation vectors, (b) execute a first focused element calculation procedure for a group of the vectors representative of an interior of a designated aperture and a second focused element calculation procedure for vectors corresponding to a boundary of the aperture, and (c) generate synthetically focused aperture elements based on the first and second procedures to provide a corresponding image.

5. The apparatus of claim 4, wherein the device includes a removable memory device encoded with the logic in the form of programming instructions.

6. The apparatus of claim 4, wherein the device includes at least a portion of a computer network.

7. The method of claim 2, wherein a first one of the two active elements is generally symmetric about a first axis, a second one of the two active elements is generally symmetric about a second axis, and the two active elements are each mounted in a housing with a base having a generally planar face operable to couple the sample for said interrogating.

8. The method of claim 7, wherein the first axis intersects a plane coextensive with the generally planar face of the base at a first oblique angle and the second axis intersects the plane at a second oblique angle.

9. The method of claim 8, wherein an internal wall portion is positioned within the housing between the first one of the two active elements and the second one of the two active elements.

10. The method of claim 9, wherein the first axis and the second axis are generally symmetric about a third axis positioned generally midway between the two active elements along the wall portion, and the third axis is generally perpendicular to the plane coextensive with the generally planar face of the base.

11. The method of claim 3, wherein the active element is positioned inside a housing, the housing includes the base, and an ultrasonic energy coupling material is positioned between the curved face of the active element and the base.

* * * * *